US007869848B2

(12) United States Patent
Proniewicz et al.

(10) Patent No.: US 7,869,848 B2
(45) Date of Patent: **\*Jan. 11, 2011**

(54) NONINVASIVE MEASUREMENT SYSTEM

(75) Inventors: Walter K. Proniewicz, Pasadena, CA (US); Dale E. Winther, La Crescenta, CA (US)

(73) Assignee: STI Medical Systems, LLC, San Diego, CA (US)

( * ) Notice: Subject to any disclaimer, the term of this patent is extended or adjusted under 35 U.S.C. 154(b) by 1002 days.

This patent is subject to a terminal disclaimer.

(21) Appl. No.: 11/552,100

(22) Filed: Oct. 23, 2006

(65) Prior Publication Data

US 2007/0100217 A1 May 3, 2007

Related U.S. Application Data

(63) Continuation of application No. 10/783,671, filed on Feb. 20, 2004, now abandoned, which is a continuation of application No. 09/489,593, filed on Jan. 21, 2000, now Pat. No. 6,853,854.

(51) Int. Cl.
*A61B 5/1455* (2006.01)
(52) U.S. Cl. ......................... 600/319; 600/476; 382/128
(58) Field of Classification Search .................. 600/310, 600/316, 318, 319, 320, 322, 323, 340, 473, 600/476

See application file for complete search history.

(56) References Cited

U.S. PATENT DOCUMENTS 5,692,504 A * 12/1997 Essenpreis et al. .......... 600/316

6,853,854 B1 * 2/2005 Proniewicz et al. ......... 600/319

* cited by examiner

*Primary Examiner*—Eric F Winakur
(74) *Attorney, Agent, or Firm*—Martin E. Hsia

(57) ABSTRACT

The noninvasive measurement system provides a technique for manipulating wave data. In particular, wave data reflected from a biological entity is received, and the reflected wave data is correlated to a substance in the biological entity. The wave data may comprise light waves, and the biological entity may comprise a human being or blood. Additionally, a substance may comprise, for example, a molecule or ionic substance. The molecule may be, for example, a glucose molecule.

Furthermore, the wave data is used to form a matrix of pixels with the received wave data. The matrix of pixels may be modified by techniques of masking, stretching, or removing hot spots.

Then, the pixels may be integrated to obtain an integration value that is correlated to a glucose level. The correlation process may use a lookup table, which may be calibrated to a particular biological entity. Moreover, an amplitude and phase angle may be calculated for the reflected wave data and used to identify a glucose level in the biological entity. Additionally, the reflected wave data may be used to determine glaucoma pressure.

The glucose level may be displayed on a monitor attached to the computer. The computer may be a portable, self-contained unit that comprises a data processing system and a wave reflection capture system. On the other hand, the computer may be attached to a network of other computers, wherein the reflected wave data is received by the computer and forwarded to another computer in the network for processing.

15 Claims, 19 Drawing Sheets

NORMAL PRESSURE

EXCESSIVE PRESSURE

LOW NODES ALC

|   | MG/DL | AMPL | PHASE |
|---|-------|---------|----------|
| 0 | 43L | 1163918 | 14035723 |
| 1 | 51L | 1118816 | 14023820 |
| 2 | 55L | 1182552 | 14035277 |
| 3 | 61L | 1140490 | 14024811 |

HIGH NODES

|    | MG/DL | AMPL | PHASE |
|----|-------|---------|----------|
| 19 | 201H | 1990270 | 14010819 |
| 20 | 213H | 1891439 | 13954830 |
| 21 | 224H | 2264146 | 14018417 |
| 22 | 235H | 2020741 | 13999554 |

LOW NODES ALC BASE

|   | MG/DL | AMPL | PHASE |
|---|-------|---------|----------|
| 5 | 72L | 1159639 | 14025629 |
| 6 | 80L | 1121179 | 14050291 |
| 7 | 99H | 1141329 | 14032470 |
| 8 | 105L | 1049958 | 13970848 |

LOW NODES ALC DOUBLE FILTER

|   | MG/DL | AMPL | PHASE |
|---|-------|---------|----------|
| 6 | 80L | 1120162 | 14067413 |
| 7 | 99L | 0 | 0 |
| 8 | 105L | 1059141 | 13990248 |
| 9 | 113L | 1097850 | 14036692 |

LOW NODES ALC BASE SMALL

|   | MG/DL | AMPL | PHASE |
|---|-------|------|-------|
| 0 | 43L | 0 | 0 |
| 1 | 51L | 0 | 0 |
| 2 | 55L | 0 | 0 |
| 3 | 61L | 0 | 0 |

LOW NODES ALC PUTBUMPS BASE

|   | MG/DL | AMPL | PHASE |   |   |   |   |   |   |   |
|---|-------|---------|----------|----|----|----|----|----|----|---|
| 0 | 43L | 1163918 | 14035723 | 5 | 27 | 37 | 4 | 66 | 72 |   |
| 1 | 51L | 1118816 | 14023820 |   |   |   |   |   |   |   |
| 2 | 55L | 1182552 | 14035277 | 13 | 16 | 24 |   |   |   |   |
| 3 | 61L | 1140490 | 14024811 | 18 | 17 | 12 | 30 |   |   |   |

FIG. 18

NONINVASIVE MEASUREMENT SYSTEM

RELATED U.S. PATENT DOCUMENTS

This application claims priority from International Application No. PCT/US99/121680, "NONINVASIVE MEASUREMENT OF BLOOD SUGAR BASED ON OPTOELECTRONIC OBSERVATIONS OF THE EYE", filed on Sep. 17, 1999, by Walter K. Proniewicz and Dale E. Winther, which is incorporated by reference herein and which claims priority to U. S. Provisional Patent Application 60/100,804, "BLOOD SUGAR MEASUREMENT THROUGH THE EYEBALL", filed on Sep. 18, 1998, by Walter K. Proniewicz and Dale E. Winther, which is incorporated by reference herein.

BACKGROUND OF THE INVENTION

1. Field of the Invention

This invention relates generally to apparatus and systems for making noninvasive tests, assessments, or determinations of substances that may be part of a human being or other biological entity and, more particularly, to software implemented apparatus and systems that noninvasively test, assess, or determine the concentration, or other features of molecular or other substances in organic matter or fluids, such as blood, existing in human beings and other biological entities.

2. Description of Related Art

There are a number of instances in which it is necessary, or at least highly desirable, to test, assess, or determine the concentration, or other features of molecular or other substances contained in organic matter or fluids, residing in biological entities, such as human beings or blood. By way of example only, blood tests are used in a variety of scientific, medical, and other applications, including a test, assessment, or determination of the level of glucose in the blood of human diabetics. Such a test, assessment, or determination is typically accomplished by an invasive procedure which, especially in the case of human diabetics, may require the drawing of blood samples a number of times each day in order to adequately monitor the level of glucose in the blood of the diabetic (i.e. the concentration of glucose in the blood—commonly called "blood sugar").

In the case of human diabetics, the invasive procedure typically involves physically withdrawing blood from the finger tips or ear lobes by using suitable lancing devices or withdrawing blood from veins by using suitable hypodermic syringes. Once withdrawn, the blood sample is then deposited within a suitable device which determines the level of blood glucose with a certain level of accuracy and reliability. Increasingly, such devices have taken the form of hand-held monitors that human diabetics use to self-test their level of glucose. Thus, conventionally, the human diabetic withdraws his or her blood by a lancing device and deposits the withdrawn blood on an indicator strip that is inserted into the monitor. The deposited blood is then analyzed and furnishes a reading of the level of glucose in the blood of the human diabetic. Correspondingly, there are various scientific and medical applications for which it may be necessary to invasively test, assess, or determine the blood glucose of even individuals who are not diabetic.

Needless to say, the use of an invasive procedure to test, assess, or determine the level of blood glucose is often painful, uncomfortable, frightening, and overall quite undesirable. One of the named inventors is a diabetic and is, therefore, all too familiar with these disadvantages. This is particularly so in the case of certain of human diabetics who are young children or are very ill or infirm individuals and who may have collapsed veins or other impediments. Invasive withdrawal of blood from human diabetics and other individuals also poses the risk of infection, unseemly scarring and the associated loss of the sensation of feeling, and the exacerbation of pre-existing chronic conditions or illnesses due to the repeated undesirable experience of invasively withdrawing blood. In fact, these disadvantages often may virtually completely dissuade a number of human diabetics from adequately testing their level of blood glucose, thereby creating a significant risk of developing serious or even life-threatening complications or even shortening their life span. The aforementioned disadvantages tend also to be exacerbated by the fact that the aforementioned conventional hand-held monitors tend to be at least nominally subject to relatively significant errors. In fact, it is relatively commonplace for two separate monitors to register differing levels of blood glucose by 15-30 percent or more.

It should, therefore, be appreciated that there exists a definite need for an apparatus and system that noninvasively, and comparatively accurately and reliably tests, assesses, and determines the level of blood glucose (i.e. the concentration of glucose in the blood) in a human being and thereby tends to eliminate or substantially reduce the pain, discomfort, trepidation, and overall undesirability associated with testing, assessing, or determining the level of blood glucose. There also exists a concomitant need for an apparatus and system that noninvasively, and comparatively accurately and reliably tests, assesses, or determines the concentration of molecular or other substances in organic matter or fluids, such as blood, existing in human beings and other biological entities.

SUMMARY

The present invention, which addresses these needs, resides in a computer software implemented system, method, apparatus, and article of manufacture that noninvasively tests, measures or otherwise assesses or determines one or more features of a molecule or other substance of a biological entity.

In accordance with one embodiment of the invention, wave data is manipulated. In particular, wave data reflected from a biological entity is received and the reflected wave data is correlated to a substance in the biological entity. The wave data may comprise light waves, and the biological entity may comprise a human being or blood. Additionally, a substance may comprise, for example, a molecule or ionic substance. The molecule may be, for example, a glucose molecule.

Furthermore, the wave data is used to form a matrix of pixels with the received wave data. The matrix of pixels may be modified by techniques of masking, stretching, or removing hot spots.

Then, the pixels may be integrated to obtain an integration value that is correlated to a glucose level. The correlation process may use a lookup table, which may be calibrated to a particular biological entity. Moreover, an amplitude and phase angle may be calculated for the reflected wave data and used to identify a glucose level in the biological entity. Additionally, the reflected wave data may be used to determine glaucoma pressure.

The glucose level may be displayed on a monitor attached to the computer. The computer may be a portable, self-contained unit that comprises a data processing system and a wave reflection capture system. On the other hand, the computer may be attached to a network of other computers, wherein the reflected wave data is received by the computer and forwarded to another computer in the network for processing.

In accordance with another embodiment of the invention, a technique for noninvasively measuring glucose concentration is provided. In particular, light waves reflected from an eye as pixels are received. The pixels are integrated to form an integrated value. Then, the integrated value is correlated to a glucose level.

The pixels may be processed to identify a center of the eye, to calculate an average brightness around the pupil of the eye, to equalize the iris of the eye using the brightness around the pupil as a baseline, to mask the pupil of the eye, and/or to remove hot spots.

In accordance with yet another embodiment of the invention, a technique for noninvasively measuring glucose concentration is provided. In particular, light waves reflected from a biological entity are received. An amplitude and a phase angle are calculated for the reflected light waves. Using the amplitude and phase angle, a glucose level is identified in the biological entity. The biological entity may comprise, for example, an eye, skin, blood, or a nail bed.

The received light waves form a matrix comprised of pixels. The amplitude is calculated by summing all of the pixels. The phase angle is calculated by summing the rows of pixels of the matrix to obtain an xGRU value, summing the columns of pixels of the matrix to obtain a yGRU value, and calculating a ratio of the xGRU value and the yGRU value. A true amplitude is calculated by subtracting a phase angle from a summation of pixels formed by the light waves.

The matrix of pixels may be processed to mask a portion of the matrix or by applying a filter to the reflected light waves. Furthermore, automatic level control is performed to modify the value of the pixels to obtain an average desired value. Automatic fine tuning is also performed.

Other features and advantages of the present invention should become more apparent from the following description of the preferred embodiments, taken in conjunction with the accompanying drawings, which illustrate, by way of example, principles of the invention.

BRIEF DESCRIPTION OF THE DRAWINGS

Referring now to the drawings in which like reference numbers represent corresponding parts throughout:

FIG. 18 illustrates various Phase/Amplitude lookup tables that have been calibrated for different settings;

DETAILED DESCRIPTION

Figure 1:
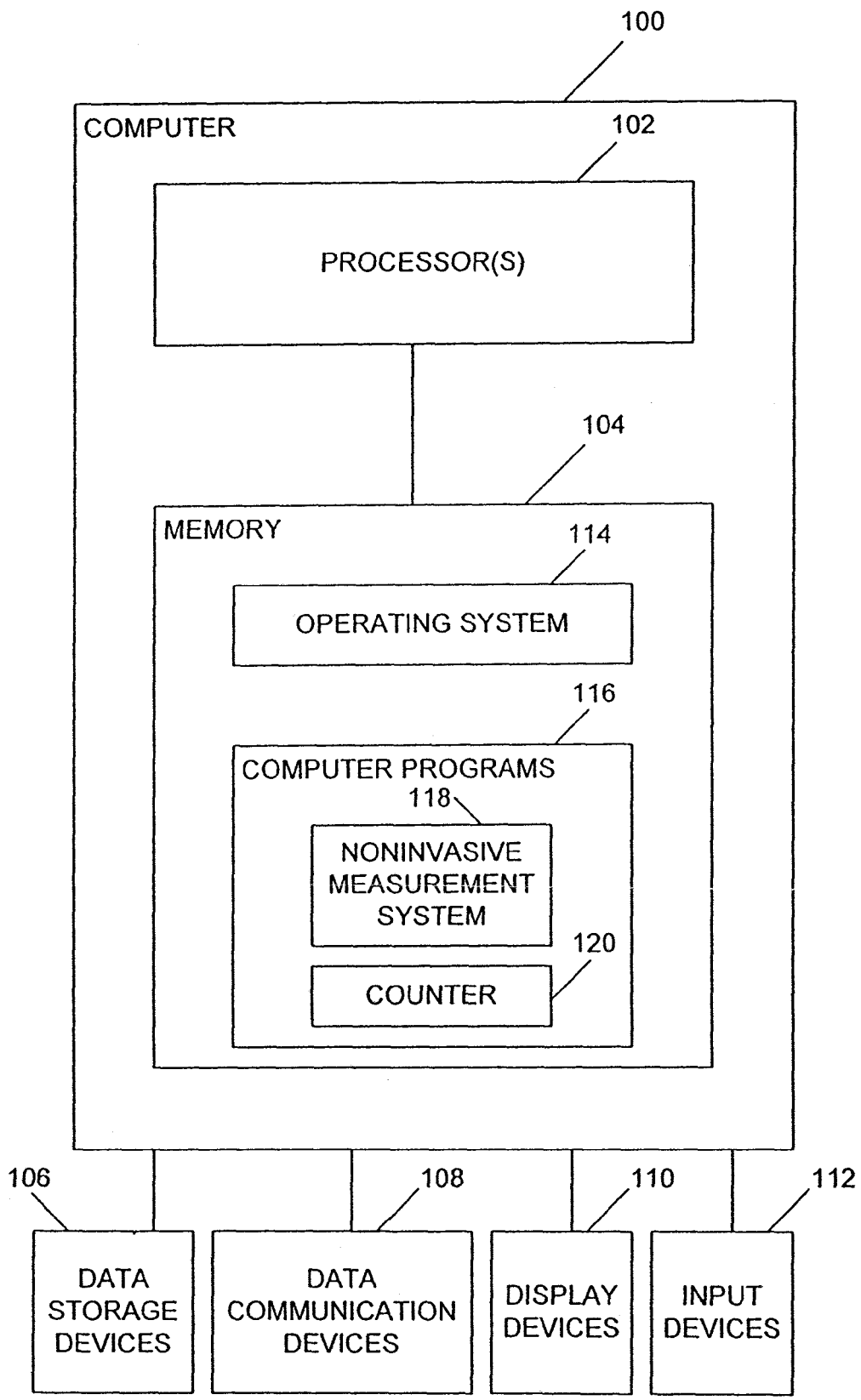
FIG. 1 is a hardware environment used to implement an embodiment of the invention.

In the following description, reference is made to the accompanying drawings which form a part hereof, and which is shown by way of illustration specific preferred embodiments in which the invention may be practiced. The following description of the preferred embodiments, taken in conjunction with the accompanying drawings, illustrates, by way of example principles of the invention. It is to be understood that other embodiments may be utilized as structural changes may be made without departing from the scope of the present invention.

A. Overview of the Noninvasive Measurement System

The present invention includes a noninvasive measurement system, method, apparatus, and article of manufacture (which will be referred to below as noninvasive measurement system), which obtains waves in the electromagnetic spectrum as input. The electromagnetic spectrum comprises a broad spectrum of wavelengths and frequencies, including visible light, infrared and ultraviolet radiation, audio transmissions, and x-rays. In the embodiments of the invention discussed below, focus will be on light waves (visible and infrared); however, it will be appreciated that the invention encompasses other types of waves that provide information appropriate to the processing described below.

The received waves are reflected off of a biological entity (e.g., human or other animal or a substance from the biological entity). In particular, the waves may be reflected off of an eye, skin, a nail, or a blood sample. The waves are received with a wave reflection capture system (e.g., a camera). The noninvasive measurement system processes the received waves and correlates the reflected waves to a substance in the biological entity. For example, in the embodiments to be described below, the reflected waves are used to determine the concentration of glucose (i.e., commonly called blood sugar) that is found in the blood of a human being.

The noninvasive measurement system has numerous advantages and applications. For example, the noninvasive measurement system may be used to diagnose patients to determine whether they have diabetes. The noninvasive measurement system may also be used as a preventive step to monitor blood glucose levels in an individual who, for example, has a history of diabetes in the family. The noninvasive measurement system may also be used to monitor diabetics who need their blood glucose levels checked multiple times a day or multiple times a week, etc. The noninvasive measurement system may also be linked with an insulin releasing system so that, when the noninvasive measurement system recognizes that insulin is needed, it can signal the insulin releasing system to release insulin. Furthermore, the noninvasive measurement system may be used to obtain glaucoma pressure.

The noninvasive measurement system may also be used to locate tumors and to locate and correct blood clots. For example, the noninvasive measurement system may be used to detect breast cancer by processing light that penetrates through flesh and is reflected.

The noninvasive measurement system may process x-rays or other high energy particles, instead of light waves, with application to various technologies using x-rays and other high energy particles (e.g., medical technologies). Moreover, the noninvasive measurement system may process ultraviolet rays to highlight or detect different types of minerals or other substances, such as ethanol present in the blood. The noninvasive measurement system can distinguish between substances based on their rotation (e.g., a glucose molecule rotates in a clock-wise direction as its density increases, while, a fructose molecule rotates in a counter-clockwise direction).

As for advantages, the noninvasive measurement system effectively eliminates need for piercing the body or otherwise obtaining blood samples, and so avoids the discomfort, fear and other detriments of using a conventional one touch glucose monitor. Additionally, the noninvasive measurement system can be manufactured as a small unit or monitor that can fit, for example, in the palm of a hand, thus allowing for use at home, or at an office or other business, or in cars, restaurants, etc.

B. Hardware Environment

In one embodiment, wave input is provided to a computer, which performs the processing of the input and displays a result on a monitor attached to the computer. FIG. 1 is hardware environment used to implement an embodiment of the invention. The present invention is typically implemented using a computer 100, which generally includes one or more processors 102, random access memory (RAM) 104, data storage devices 106 (e.g., hard, floppy, and/or CD-ROM disk drives, etc.), data communications devices 108 (e.g., modems, network interfaces, etc.), display devices 110 (e.g., CRT LCD display. etc.). and input devices 112 (e.g., camera, video recorder, mouse pointing device, and keyboard). It is envisioned that attached to the computer 100 may be other devices, such as read only memory (ROM), a video card, bus interface, printers, etc. Those skilled in the art will recognize that any combination of the above components, or any number of different components, peripherals, and other devices, may be used with the computer 100.

The computer 100 operates under the control of an operating system (OS) 114. The operating system 114 is booted into the memory 104 of the computer 100 for execution when the computer 100 is powered-on or reset. In turn, the operating system 114 then controls the execution of one or more computer programs 116, such as a noninvasive measurement system 118 and a counter 120, by the computer 100. The present invention is generally implemented in these computer programs 116, which execute under the control of the operating system 114 and cause the computer 100 to perform the desired functions as described herein. Although shown as separate from the noninvasive measurement system 118, one skilled in the art would recognize that the counter 120 may be part of the noninvasive measurement system.

The operating system 114 and computer programs 116 are comprised of instructions which, when read and executed by the computer 100, causes the computer 100 to perform the steps necessary to implement and/or use the present invention. Generally, the operating system 114 and/or computer programs 116 are tangibly embodied in and/or readable from a device, carrier, or media, such as memory 104, data storage devices 106, and/or data communications devices 108. Under control of the operating system 114, the computer programs 116 may be loaded from the memory 104, data storage devices 106, and/or data communications devices 108 into the memory 104 of the computer 100 for use during actual operations.

Thus, the present invention may be implemented as a method, apparatus, system, or article of manufacture using standard programming and/or engineering techniques to produce software, firmware, hardware, or any combination thereof. The term "article of manufacture" (or alternatively, "computer program product") as used herein is intended to encompass a computer program accessible from any computer-readable device, carrier, or media, including the internet. Of course, those skilled in the art will recognize many modifications may be made to this configuration without departing from the scope of the present invention.

Those skilled in the art will recognize that the environment illustrated in FIG. 1 is not intended to limit the present invention. Indeed, those skilled in the art will recognize that other alternative hardware environments may be used without departing from the scope of the present invention. For example, the computer 100 may be a portable, self-contained unit that comprises a data processing system and a wave reflection capture system (e.g., a camera). The computer 100 may be about the size of the palm of an average individual's hand. Moreover, the noninvasive measurement system 118 may be incorporated into different apparatus than those illustrated herein. Additionally, the counter 120 may comprise software that is structured to limit the use of the noninvasive measurement system over a specified period of time (e.g., one year) or for a specified number of uses (e.g., 1000 uses).

Figure 2:
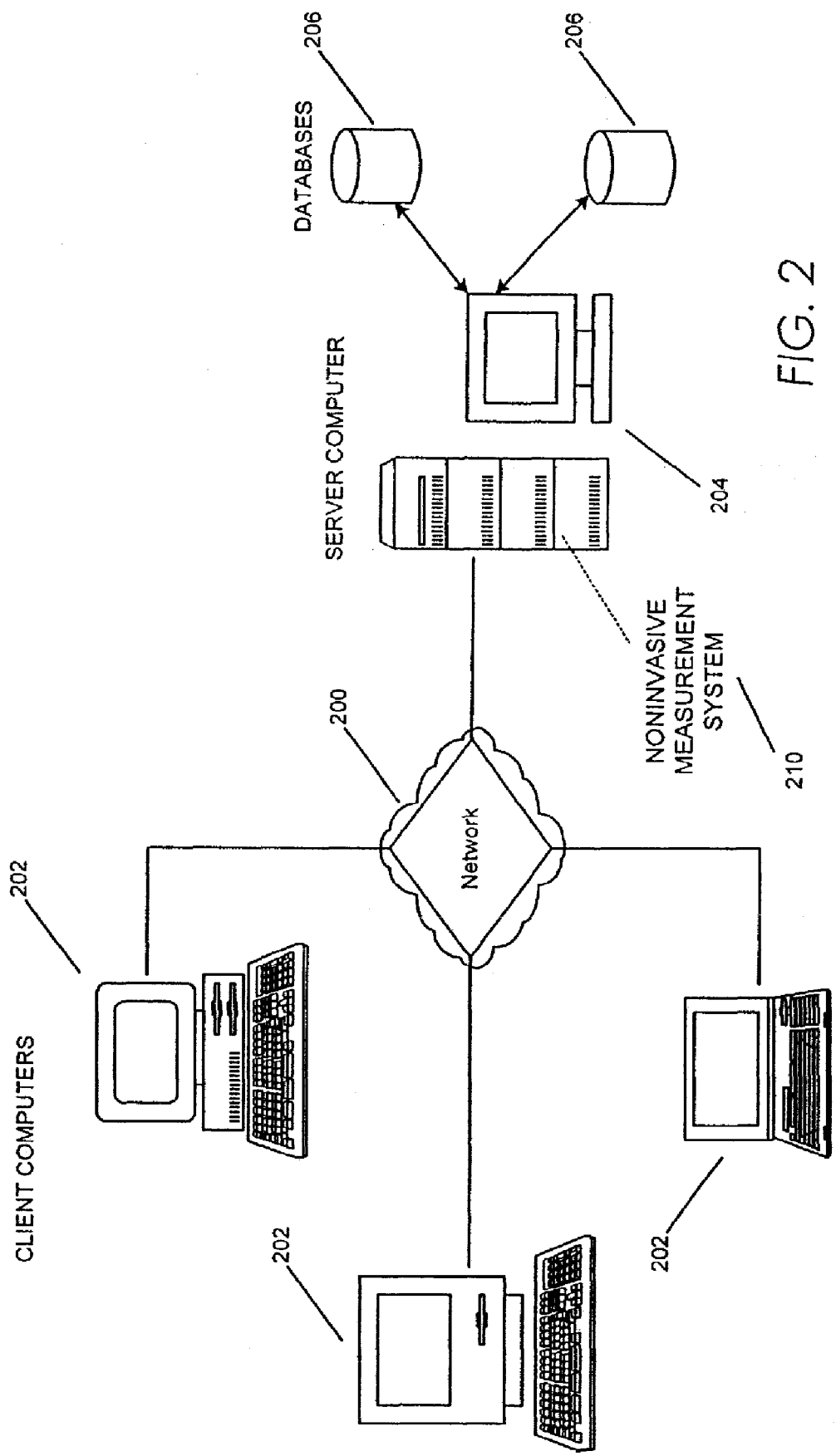
FIG. 2 is a schematic illustration of the hardware environment of an embodiment of the present invention, and more particularly, illustrates a typical distributed computer system.

In another embodiment of the invention, wave input is provided to a client computer, which transmits the data to a server computer for analysis. FIG. 2 is a schematic illustration of the hardware environment of an embodiment of the present invention, and more particularly, illustrates a typical distributed computer system using a network 200 to connect client computers 202 executing client applications to a server computer 204 executing software and other computer programs, and to connect the server system 204 to data sources 206. A typical combination of resources may include client computers 202 that are personal computers or workstations, and a server computer 204 that is a personal computer, workstation, minicomputer, or mainframe. These systems are coupled to one another by various networks, including LANs, WANs, SNA networks, and the Internet. Each client computer 202 and the server computer 204 additionally comprise an operating system and one or more computer programs.

A client computer 202 typically executes a client application and is coupled to a server computer 204 executing one or more server software. The server software may include a noninvasive measurement system 210. The server computer 204 also uses a data source interface and, possibly, other computer programs, for connecting to the data sources 206. The client computer 202 is bi-directionally coupled with the server computer 204 over a line or via a wireless system. In turn, the server computer 204 is bi-directionally coupled with data sources 206. The data sources 206 may be geographically distributed.

The operating system and computer programs are comprised of instructions which, when read and executed by the client and server computers 202 and 204, cause the client and server computers 202 and 204 to perform the steps necessary to implement and/or use the present invention. Generally, the operating system and computer programs are tangibly embodied in and/or readable from a device, carrier, or media, such as memory, other data storage devices, and/or data communications devices. Under control of the operating system, the computer programs may be loaded from memory, other data storage devices and/or data communications devices into the memory of the computer for use during actual operations.

Thus, the present invention may be implemented as a method, apparatus, system, or article of manufacture using standard programming and/or engineering techniques to produce software, firmware, hardware, or any combination thereof. The term "article of manufacture" (or alternatively, "computer program product") as used herein is intended to encompass a computer program accessible from any computer-readable device, carrier, or media, including the internet. Of course, those skilled in the art will recognize many modifications may be made to this configuration without departing from the scope of the present invention.

In one embodiment, in a networked environment, part or all of the noninvasive measurement system may reside at the server computer. An individual may transmit an image of, for example, their eye at the client computer to the server computer. The noninvasive measurement system would process the image data and return a blood glucose level (i.e., commonly referred to as "blood sugar") to the client computer, for use by the individual.

Those skilled in the art will recognize that the exemplary environment illustrated in FIG. 2 is not intended to limit the present invention. Indeed, those skilled in the art will recognize that other alternative hardware environments may be used without departing from the scope of the present invention.

C. Noninvasive Measurement of Glucose Concentration in an Eye

The noninvasive measurement system determines the concentration of glucose in blood, without the need for invasive procedures. The noninvasive measurement system can determine glucose levels by analyzing light waves reflected from the eye.

A handheld illumination and imaging system is used to take blood glucose measurements. The system advantageously operates by integrating the reflected light from the iris portion of the eye, rather than from the retina. Numerous anterior blood vessels present a means of directly observing bloodstream content with exterior optical techniques.

Glucose accumulations in this area produce a change in the intensity of reflected light. The more glucose present, the higher the level of reflected light. The concentration of glucose in this area can potentially change in seconds.

This change in light reflection is too small to be seen with normal observation techniques. The ability to measure light intensity changes as small as 1 part in 10,000 is required to detect blood glucose changes.

A CCD camera images the eyeball and the image is digitized. These data are processed to remove the pupil pixels. Only the iris pixels are used as representative of glucose levels as such, but as explained elsewhere the pupil pixels are used to develop baseline and illumination levels.

The iris pixels are integrated (summed) to produce a single intensity number. This is sometimes called the "integrated data number" or IDN for short; it is interchangeably designated "GLU", for glucose value.

The IDN (or GLU) value can be calibrated by removing image scene and illumination discrepancies. It can be further calibrated to an individual patient to produce an extremely accurate IDN-to-blood-glucose (GL or glucose level) correlation. Repeatable scene geometry is also very desirable for accurate measurements.

As mentioned above, the primary IDN calibration technique uses pupil reflection and geometry data. Changes in input light levels are detected by sensing pupil brightness.

The average reflected intensity level of the pupil is used as the dark-level baseline for IDN processing. Only intensities that are higher than that of the pupil are integrated into the IDN.

This is a scene-to-scene automatic light level calibration. If the scene light level goes up, so do the levels of the pupil and -iris. The pupil level offsets the higher iris level and preserves the scene-to-scene relative brightness. This guarantees that only glucose-level increases will cause measured intensity increases.

The following pseudo-code reflects the processing performed by the noninvasive measurement system. Further details about each of these processing steps will be discussed below.

1. image the eyeball
2. find the center of the pupil
3. calculate the average brightness around the pupil center
4. mask out the pupil region of the eye
5. equalize the iris image using the pupil brightness as a level baseline
6. remove hot spots if present
7. integrate all of the processed iris pixels
8. search a lookup table to find the closest IDN-to-GL correlation
9. display the imputed glucose number in GL C.1 Image the Eyeball Imaging the eyeball refers to taking a picture of the eye. In particular, the noninvasive measurement system transmits broad spectrum visible and near infrared light to the eye. The transmitted light can come from different sources, such as tungsten light, light emitting diodes (LEDs), and white or colored light bulbs.

The noninvasive measurement system receives back a portion of the waves (i.e., some of the waves are absorbed). In one embodiment, the portion received back and used comprises' infrared waves. As blood glucose changes, the amount of reflected light changes. This is believed to be due to the fact that glucose is a substance that reflects light and that may increase. On the other hand, blood absorbs light. Therefore, as glucose increases in the blood, more light is reflected from the glucose substance, and less is absorbed by the blood.

The noninvasive measurement system comprises an apparatus that holds a light source directly in front of the camera lens. The light source is made to shine onto the eye from the geometric center of the camera lens. This results in even illumination of the eye, eliminating reflections and hot spots.

Two additional effects are created by this central-illumination geometry:
1. the light source becomes a visual centering target for the patient; and
2. the light source becomes a peak amplitude point for finding the image center.

After transmitting light toward the eye, the noninvasive measurement system takes a picture of the eye. This results in the light waves that are reflected from the eye passing through a lens system. The lens focuses the waves on the surface of a CCD detector. The waves strike with different amounts of energy and different angles. This leads to a picture that is represented by pixels of the CCD detector. With an 8-bit CCD detector, each pixel value falls in the range of 0-255, with each value in the range corresponding to a different shade of gray.

A CCD is a charge coupled device whose semiconductors are connected so that the output of one is the input to another. A CCD camera is based on electronic chips called CCD sensors. These components are sensitive to light and allow pictures to be digitized and stored in computers. A CCD chip is an array of light-sensitive capacitors. The capacitors are charged by the electrons generated by the light. Each light element that reaches the CCD array displaces some electrons that are providing a current source. The current sources are localized in small delimited areas called pixels. The pixels form a CCD matrix.

In particular, the surface layer of this chip contains a grid, and each cell of the grid is a silicon diode which builds an electrical charge proportional to intensity and time light falls on it. A discharging circuit is connected to all cells. Behind these cells is a matching grid of pixels (i.e., a CCD matrix). Each cell stores an analog voltage rather than an off-on (binary) value. The storage capacity of a pixel is also referred to as a well, and the electric charge storage capacity of a typical pixel can be several hundred thousand electrons.

Generally, the charges are converted to voltages through an analog to digital (A/D) converter. In the A/D converter, the electric charge of a pixel is converted to an 8-bit number ranging from 0-255. The 8-bit number is referred to as a pixel data number. The pixel data number represents the converted amplitude of each pixel. The noninvasive measurement system uses a black & white CCD television (TV) camera and a personal computer. A fully portable version of the noninvasive measurement system that fits in the palm of one's hand is presently possible. A CCD camera uses 8 digits to represent the amount of light energy that hits the CCD surface. Because 8 digits are used to represent the amount of light energy, it can express brightness in 256 (0-255) levels.

In an alternative embodiment, a filter is used. In particular, a band pass filter is placed in front of the camera lens and behind the light. This filters light to eliminate most of the visible spectrum. In yet another alternative embodiment in which a filter is used, the light waves are cut off just before or after a particular wavelength value.

In an alternative embodiment, a digital camera is used. With a digital camera. 312 bits are used to represent the amount of light energy that hits the CCD surface. The 312 bits are used to represent the amount of light energy ranges from 0 to 4096 (rather than 0 to 255). This leads to better resolution of the light energy.

C.2 Find Center of Pupil

The next processing step is to find the center of the pupil. The noninvasive measurement system centers the pupil on the image. In particular, while taking the picture, the image of the picture is transmitted by the camera to a computer having a monitor. Prior to "snapping" a picture for use in calculating a blood glucose value (i.e., concentration), the noninvasive measurement system enables the eye to be adjusted relative to the camera lens to physically place the eyeball in the center of the picture. Additionally, once the picture is taken, the pixels of the CCD matrix are stored in an array, sequentially, by row order. The center of the array identifies the center pixel of the picture. That is, the noninvasive measurement system finds the energy center.

Having found the center of the pupil, the noninvasive measurement system also performs the following processes: zeroes-out the area within the light source, to eliminate the light source from the pupil image, determines the eye registration within the camera frame and calculates the useful image area, grows a pupil mask from the light source centerpoint and use it to cover the pupil area in the image, and captures the area under the aligned pupil mask for the dark-level calibration. These are discussed in more detail below.

C.3 Calculate the Average Brightness Around the Pupil Center

Next, the noninvasive measurement system calculates the average brightness around the pupil center. The noninvasive measurement system treats the pupil as a black dot. After finding the center of the pupil, the noninvasive measurement system takes 150 pixels horizontally and vertically from the center of the pupil and calculates an average brightness (i.e., this is the sum of the values of the pixels divided by the number of pixels summed). This average is the average brightness of the center of the pupil. This will be used as a baseline value for further calculations.

C.4 Mask Pupil Region

The noninvasive measurement system masks out the pupil region of the eye. The noninvasive measurement system masks a central area, sufficient to cover a pupil. Different people have different size pupils. The area to be masked was a "sufficiently large" amount that would cover the pupil of most individuals. For one embodiment, this "sufficiently large" value was experimentally found to be about 90,000 square pixels. The noninvasive measurement system forms a sufficiently large box around the pupil and sets the pixels in this box to zero. The pupil is then a dark level reference. The masking process results in excluding the pupil from further processing. Thus, the noninvasive measurement system defines a number of pixels in an iris that are to be processed.

Although different individuals have different sized pupils, by keeping the mask the same size across individuals, the noninvasive measurement system processes approximately the same number of pixels for an iris across different individuals. If changes in pupil diameter between individuals and pupil centering are not held constant, the total number of iris pixels available for integration will change. To control these effects, a software pupil mask is employed. This zeroes-out a fixed region around the pupil.

The software pupil mask is larger than the largest pupil diameter and covers pupil-centering errors. Some iris pixels may be zeroed in the process, but all image frames are treated in the same way. The pupil mask is preferably always the same size, and therefore all image frames contain the same number of iris pixels. The geometric distortions due to pupil variations are eliminated.

In an alternative embodiment, the mask size may be determined based on an individual's own pupil size.

C.5 Equalize the Iris Image Using the Pupil Brightness as a Level Baseline

The noninvasive measurement system also applies image contrast equalization, also referred to as stretch. This causes pixels to fill the complete dynamic range of pixel data. The pupil baseline data is applied to this process, permitting only the pixels that are brighter than the pupil to be remapped. As a result, further processing takes place using data that have been scene-level-biased and equalized to a full amplitude range.

Stretch takes an 8-bit number (i.e., the pixel data number) representing pixel data and remaps the pixel data number to the full dynamic range of 0-255. The pupil, which has-been masked, contains all zeroes. So, for example, if the brightest pixel is 95, the noninvasive measurement system may map the values 0-95 to 0-255, with 0-5 mapping to zero and 90-95 mapping to 255. Thus, several values (e.g., 12, 13, and 14) can be mapped to the same number (e.g., 56). This resolves small variations in the scene in the eye (e.g., tearing).

A technique called auto-stretch is used, which is well-known in the image processing area. This compensates for small changes in illumination (e.g., the light source is drifting or if room light gets in as well as light transmitted by the noninvasive measurement system). This also deals with the problem in which light does not fall on an eye the same for sequential pictures. Consistency is needed for better accuracy of the results. By weeding out variables, such as changes in light, the noninvasive measurement system can detect that the changes in pixels represents a change in the level of glucose in the blood, rather than other changes.

Additionally, the noninvasive measurement system may use a gamma stretch, which is a non-linear stretch. The gamma stretch takes care of the effects of bright sunlight. In particular, a gamma stretch amplifies more when there is darkness, and less when there is bright light. Most cameras have gamma circuits. For the noninvasive measurement system, the hardware gamma stretch was turned off. However, in one embodiment, a controlled software gamma stretch is used to enhance specific regions of the return levels (e.g., the bottom or top level of the picture).

C.6 Remove Hot Spots If Present

Hot spots are extraneous illuminations of light (e.g., outside light) or uneven illumination of the eye (e.g., light source is not over the center of the eye or there is a reflection of the light). Once illumination set up, with the noninvasive measurement system, the illumination does not change. Therefore, the location of hot spots have been found by experimentation with light (e.g., can see light source reflected in the eye). This leads to customized masking based on a particular illumination system.

To remove known hot spots, the noninvasive measurement system draws a box around the hot spot and zeroes the pixels in the box. The size of the box was experimentally found and differs based on the illumination system used.

That is, good light source diffusion is needed to prevent hot spots. Additionally, the noninvasive measurement system performs hot-spot removal with software masks. Thus peak signal amplitudes are removed before the integration process.

The noninvasive measurement system finds the light (seen as a hot spot in the center of the pupil) and performs a position alignment based on its location.

C.7 Integrate All of the Processed Iris Pixels

The noninvasive measurement system adds up the pixels that form the picture of the eye. Because the pupil has been masked (i.e., set to zeroes), the pixels that are added are those of the iris. The sum of the pixels is referred to as an "integrated data number" or IDN. The IDN value is interchangeably designated "GLU", for glucose value.

C.8 Search a Lookup Table to Find the Closest IDN-to-GL Match

The sum of the pixels provides an integrated data number (IDN). The noninvasive measurement system maps the IDN to a glucose level (GL) using an IDN-to-GL lookup table. It will be appreciated that the look up table effectively provides a correlate of glucose concentrations. That is, it provides ranges of values that are correlated to different glucose concentrations.

The process of converting the IDN to a true glucose measurement requires a simple lookup operation to verify that the result is within a predetermined error band. The correlation from IDN to milligrams per deciliter (mg/dl) can be seen in the following formula An program entitled "Average" (discussed in Section C.12 below) determines a minimum and maximum IDN value by comparing IDN values for a series of images of the same eye, taken in succession. Similarly, the program determines the minimum and maximum GL values by comparing GL values for the same series of images. The program also determines the actual glucose level using the lookup table.

$$IGN = \frac{IDN_{max} - IDN_{min}}{GL_{max} - GL_{min}} \cdot GL + IDN_{min}.$$

These terms are defined as follows.

IGN=implied glucose number
$IDN_{max}$=highest possible IDN (integrated data number)
$IDN_{min}$=lowest possible IDN
$GL_{max}$=highest possible glucose value (in mg/dl)
$GL_{min}$=lowest possible glucose value (mg/dl)
GL=actual glucose value (mg/dl)

Inserting a milligram/deciliter value in GL yields its equivalent IDN value in IGN.

Going from IDN to GL is accomplished by searching or hashing a lookup table. When the IDN value is equal or almost equal to a bounded IDN table value, GL is retrieved from the table and output as the glucose reading.

The IDN lookup table is produced by averaging multiple calibrated IDN samples for known glucose values. A fixed error range is based on a plus-or-minus deviation percentage from the average IDN. This is preferably done for all available glucose numbers. Because it is difficult to obtain values for every glucose number, values between known samples can be interpolated to create a complete table. In one embodiment, a limited range of measurements were used to produce a small example conversion table, which is shown above. One skilled in the art would recognize that a larger database of images and experimental data may be used to create an IDN-to-GL lookup table for a broader range of glucose measurements.

The IDN-to-GL lookup table has columns for a minimum and maximum range of the IDN number. Each minimum to maximum range maps to a GL number. The IDN-to-GL table was calibrated by experimenting on an individual, Walter K. Proniewicz. Each experiment consisted of using a camera to obtain an image of an eye of the individual, calculating an IDN value, and obtaining a GL value for the individual using the noninvasive measurement system. Traditional (one-touch) glucose monitors were used to verify the validity of the glucose concentration found via the technique of this invention. The IDN-to-GL lookup table was built by identifying, by this experimentation a GL value that correlated to ranges of the DN value.

The following is the IDN-to-GL lookup table that was calibrated for the noninvasive measurement system:

| MIN IDN | MAX IDN | GL |
|---|---|---|
| 23092848 | 23155106 | 38 |
| 23221033 | 23310529 | 45 |
| 25909009 | 25999999 | 84 |
| 23350883 | 23540368 | 109 |
| 23500534 | 23851841 | 175 |
| 23978300 | 24034595 | 194 |
| 24047870 | 24052409 | 244 |

Experiments were performed on more than 20 other people. For the experiment, each person was tested with the noninvasive measurement system and, for verification, tested with a traditional (one-touch) glucose monitor that samples blood. Each person then increased their blood glucose levels (e.g., by eating donuts). Then, each was again tested with the noninvasive measurement system and, for verification, tested with a traditional (one-touch) glucose monitor that samples blood.

The twenty people included were all adult subjects with one additional known diabetic. Their 18 men and 2 women. All subjects were caucasian. A large variation in pupil sizes was noted. Eye color was not recorded. Additional system sensitivity and accuracy can be obtained by capturing multiple frames and summing their IDNs together. Changes due to small movements of the eye are thereby averaged out. Digitally summed IDN also increase effective integration time, resulting in a larger dynamic range.

C.9 Display the Imputed Glucose Number in GL

The noninvasive measurement system displays the GL value on a display device connected to the computer, such as a computer monitor. The combined result of the camera/computer arrangement is a numeric output that displays blood-glucose levels in units of milligrams/deciliter, on a computer screen or small LCD display.

C.10 Details of Apparatus

A high-resolution black-and-white digital video camera assembly (FIG. 3) uses a charge-coupled detector (CCD) array as a sensor. The camera includes a body 310 for housing the CCD array, a mounting section 311 with an attachment thread 329, a camera sync connector 312, and a video-out connector 313.

It will be understood that all of the details presented here relate to experimental prototypes that have been built and tested. Representative dimensions for the assembly follow.

| REFERENCE NUMBER IN DRAWINGS | VALUE (INCHES) |
|---|---|
| 321 | 2.18 |
| 322 | 3.75 |
| 323 | 0.75 |
| 324 | 0.69 |
| 325 | 0.75 |
| 326 | 2.38 |
| 327 | 1.25 |
| 328 | 1.40 |

An extension tube 314 holds a 1:1.4 lens 315, making the focal length approximately 2½ cm (one inch). The purpose of the extension tube is to maximize the amount of data from the iris 432 (FIG. 4) of the eye 430 and limit, to zero, the amount of white of the eye.

At the beginning of testing "Snappy™" shots were selected. A Snappy devise, manufactured by Play Inc., is an image-capture card for a personal computer (PC). It captures a one-thirtieth-second frame from a moving image and stores it for future analysis.

Approximately forty percent of all frames were lost because of movement of the eye, reflections, and exposed white of the eye. The frames used are advantageously similar; the total digital numbers are preferably as close to each other as possible.

To produce optical data for the camera, a small light source 433 (FIG. 2) directs light 434 toward the center of an eye 430, and reflections 435 from the pupil 431 and iris 432 traverse the lens 315 to the CCD camera 310. Note that no optical dispersing or wavelength-selecting device is included.

Thus the CCD camera 310 sees the reflected light 435 from the eye. Raw video data 437 go to a digital interface 438, which responds with corresponding digital data 439 that proceed into a computer 440. The computer may be a portable, self-contained unit that comprises a data processing system (e.g., computer 440 or a microprocessor) and a wave reflection capture system or a receiver that receives wave data (e.g., camera 310).

Figure 3:
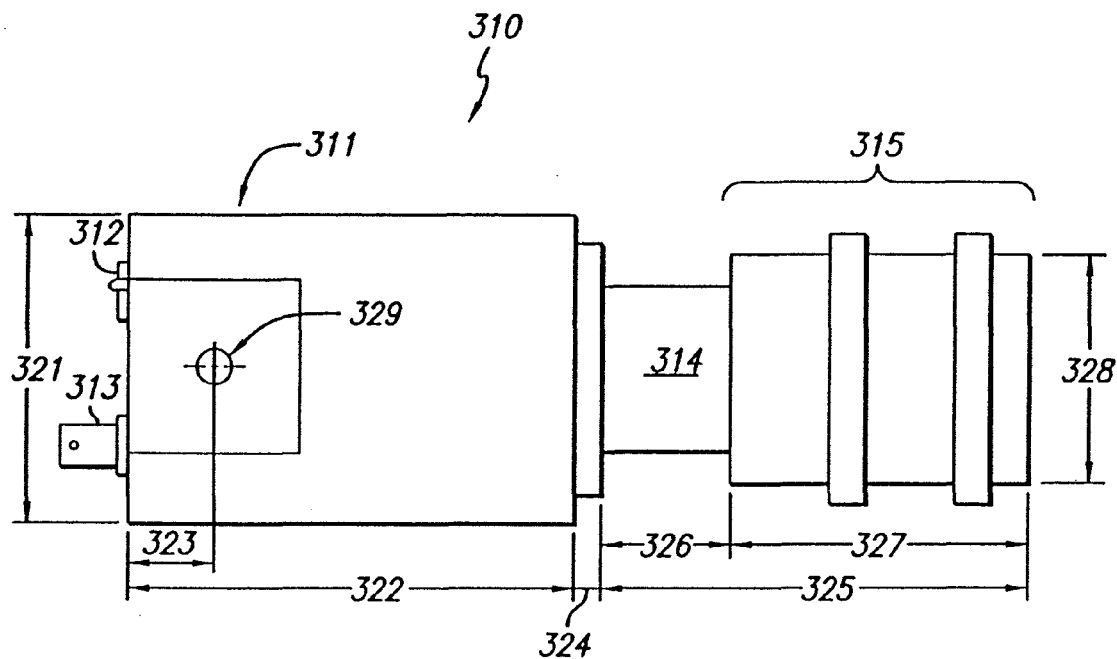
FIG. 3 is a schematic diagram, in plan, of a CCD camera assembly used in one embodiment of the invention, and contemplated for adaptation into a commercial unit.
Figure 4:
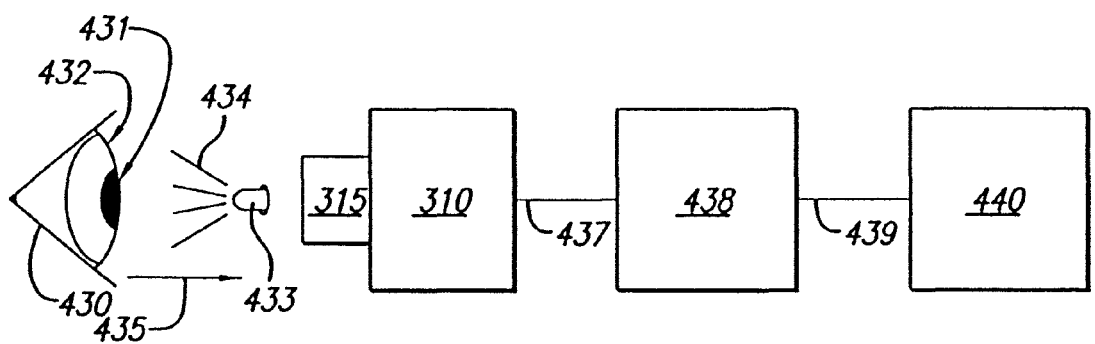
FIG. 4 is a block diagram showing the image input data stream derived from optoelectronic measurements of an eye, using the FIG. 3 camera assembly in a centralized illumination arrangement.
Figure 5:
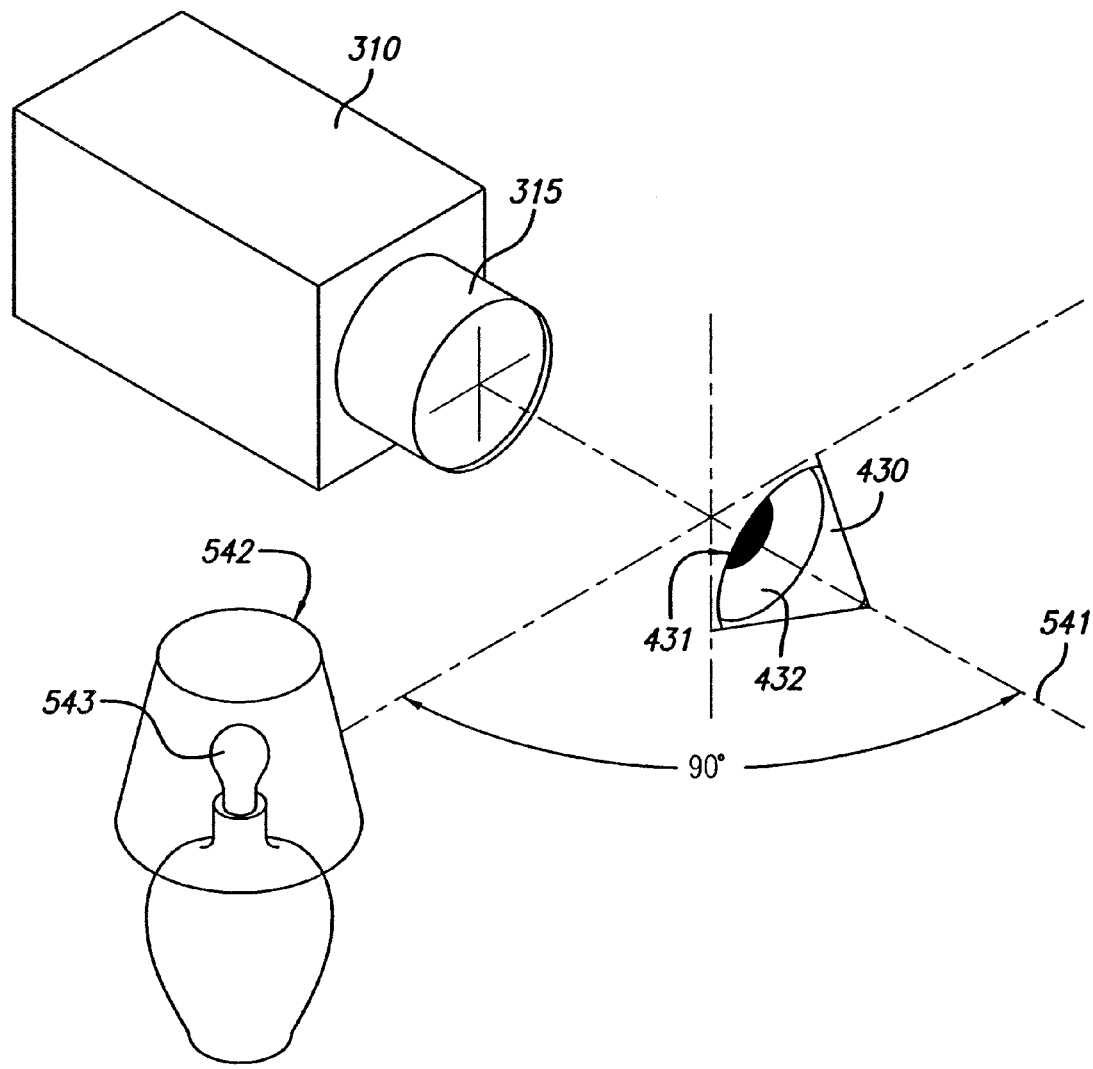
FIG. 5 is an isometric view of a representative illumination geometry, one of several variations, illustrating a diffuse-illumination approach.

The central-illumination arrangement of FIGS. 3 and 4 was the successor to numerous earlier efforts based instead on diffuse illumination of and data collection from the eye. In the first successful, repeatable one of those (FIG. 5), light from a forty-watt incandescent party bulb 543 was integrated by flat white paint on the walls of the room itself—essentially a large integrating-sphere concept.

The light was arranged to approach the eye 430 at a right angle to the optical axis 541 between the lens and the eye, to minimize formation of reflections and shadows. To minimize the problem of hot spots and resulting high data counts, mostly caused by bare exposed lightbulbs, the illumination was passed through a diffuser 542—created from a plain white paper cylinder placed around the light source.

Figure 6:
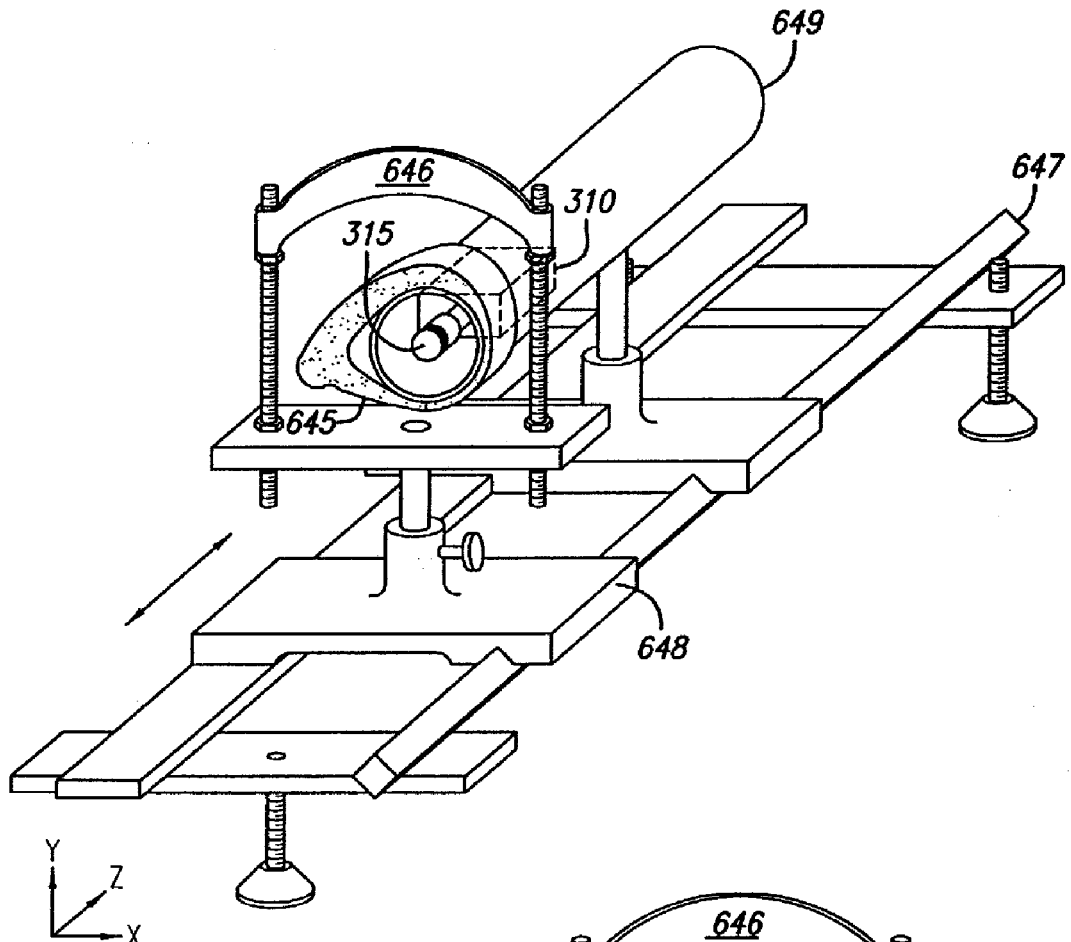
FIG. 6 is a perspective view of an optical bench, particularly including a foam ocular and a forehead rest.
Figure 7:
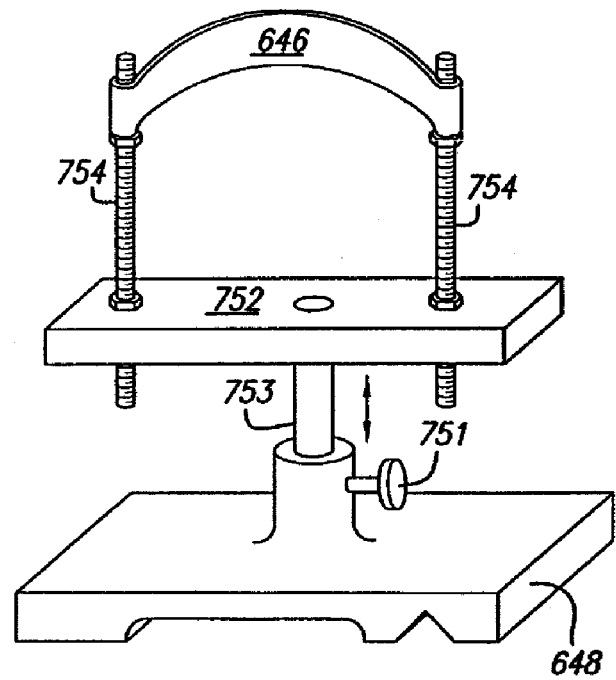
FIG. 7 is a more detailed view shown in FIG. 6.

To lessen the difficulties of repeating frames and holding the CCD camera steady, and to shield and eliminate reflections, an optical bench with a foam ocular 645 (FIG. 6) was built. In addition, a headrest (FIG. 7) helps stabilize the eye.

The optical bench, three feet long, was fashioned from two aluminum rails 647 (FIG. 6)—a rectangular one, lying horizontal, and a square bar turned on the diagonal so that one corner fits into corresponding notched grooves in the base 648 of the headrest and in the base of the camera support. The bar allows movement only along the z-axis (i. e., longitudinally). This geometry also allows setting of distances between the headrest (i. e., the eye position) and the camera.

The support stand allows up-and-down (y-axis) adjustment by means of a vertical rod with an adjustment knob. The two rails are kept parallel by being mounted on two eight-inch crossbars with three legs made from machinist jackscrews. One leg is attached to the center of the cross-bar, the other two legs are attached at opposite ends of the other crossbar, thereby allowing leveling in a classical manner.

The headrest is mounted to a sliding aluminum base 648, to support two one-foot-long threaded vertical rods 754 holding a curved aluminum forehead piece 646. The whole mechanism is mounted on a centered vertical support rod 753. A crossbar 752 supports a subject's chin on a soft pad (not shown), and the forehead rests against the forehead piece 646 to stabilize the head. Adjustment and locking are facilitated by an adjustment screw 752.

The CCD camera is also mounted on a support rod, set in a commercial support stand. The rod is attached to the camera, which is inside a tubular cardboard light shield 649 (made from a cardboard mailing tube). A trapdoor allows for adjustments to the camera with two camera-support screws through the tubular shield, centering the camera in the shield.

The tube is four inches in diameter and fourteen inches long. The trapdoor is eight inches long and sections out half of the tube, starting one inch back from the front. The camera lens face is flush with the end of the tube. The interior of the tube is painted flat white.

Various other experimental setups included some geometries with two tubes—one for each eye, with an eye-tracker disc placed in front of the eye not being sampled. In one embodiment, a system with no ocular lens and in which the nondata eye is exposed is used.

Figure 8:
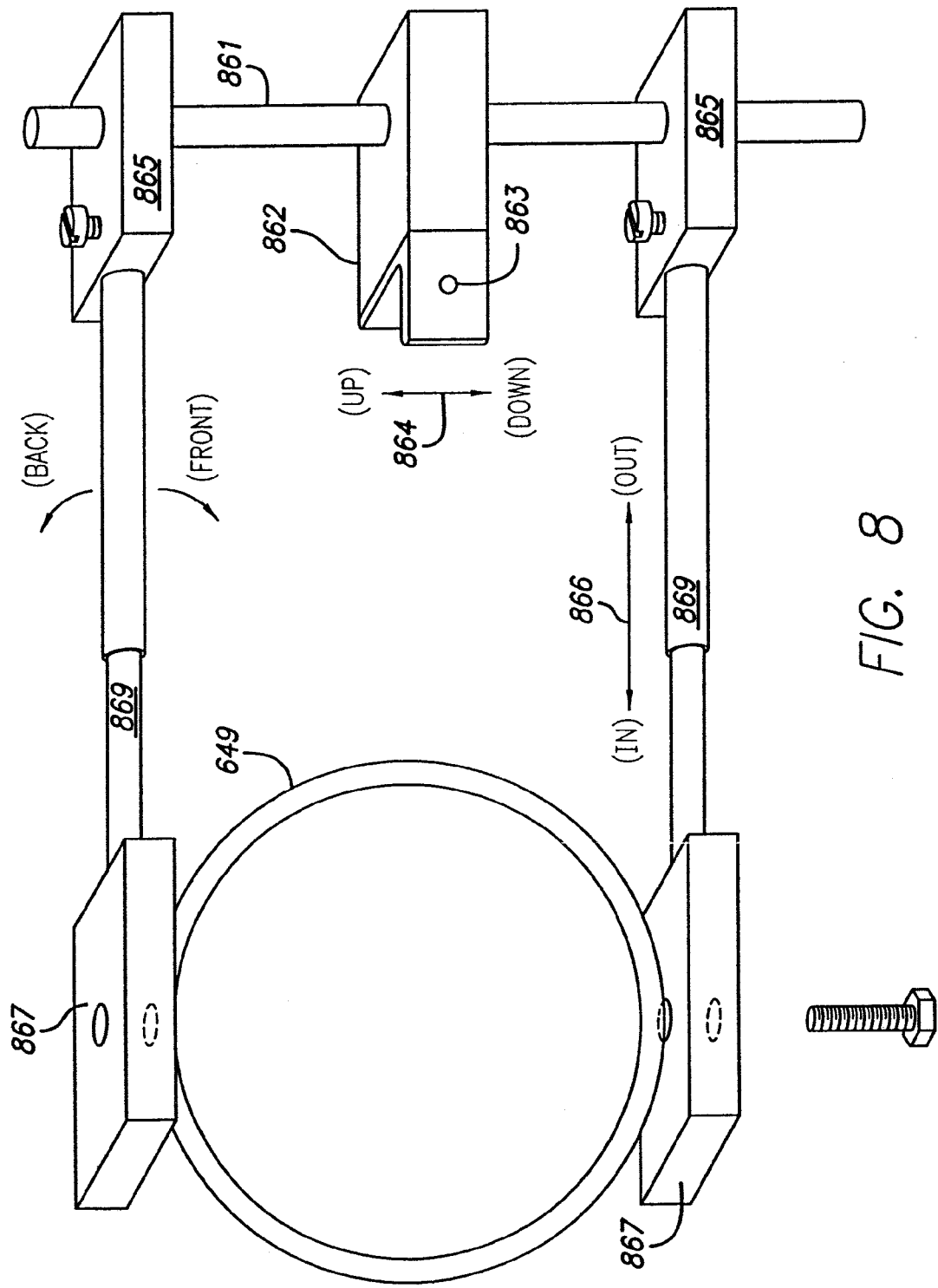
FIG. 8 is a perspective view of an early eye-tracking system.

In one experimental setup, a pair of slip-tube swing arms 869 (FIG. 8) fixed to the camera mounts—above and below the tubular shield 649—held a vertical rod 861 on which a block 862 slides up and down 864, carrying a light-emitting diode (LED) 863. The LED served as the light source for central illumination. The slip tubes enabled horizontal adjustments 866, and the LED block vertical movement 864.

The next development in experimental progression eliminated use of a mechanical eye-tracker. A video monitor is used to show real-time video of the eye being viewed for data collection.

The subject views his or her own eye on the monitor, and can rapidly correct for positioning of the eye, thus minimizing the amount of white of the eye showing—and allowing for detection of unwanted reflections. Looking at a real-time video is faster and easier than doing eye-tracking using the mechanical tracking system.

Selected single frames were stored using a frame grabber or Snappy™ image-capture card. In this process, data collection took a long time because flames with high data error—usually half of the frames taken—had to be discarded.

Next a video recorder was employed. For experimental purposes the start time, lamp color, filters, blood glucose values, commentary and end time were annotated audibly.

Four to five minutes of video data were taken continuously. The end result was thousands of frames (at a frame rate of thirty per second) from which to handpick later.

Good frames could be selected, saving a great amount of time. This is also proved that the accuracy and repeatability were very high, much better than current blood-glucose meters on the market.

Figure 10:
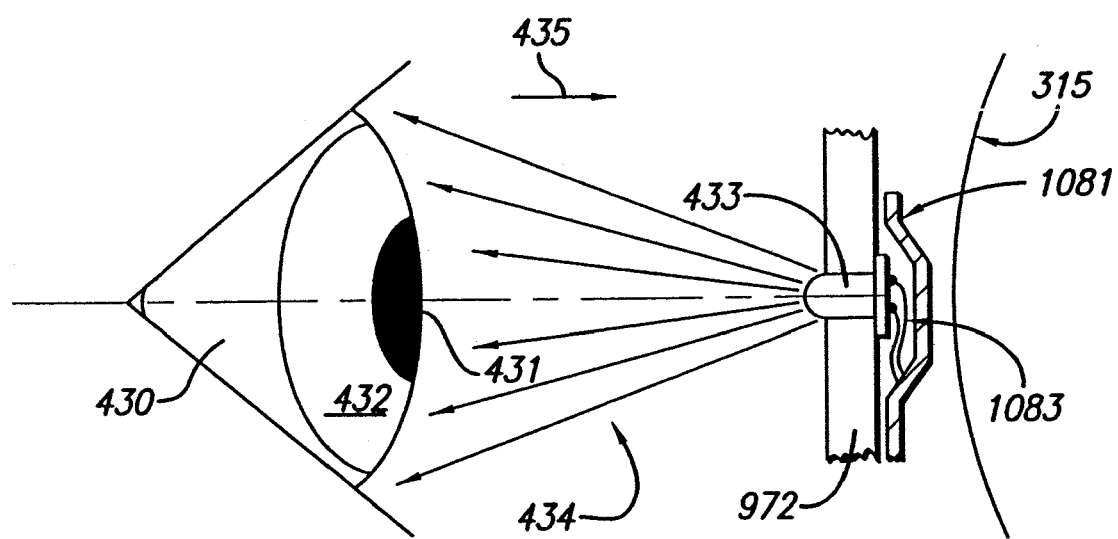
FIG. 10 is an enlarged view of the FIG. 9 bezel, shown with light source and eye, in longitudinal elevation generally along the system centerline.

Experimental work also explored numerous illumination arrangements with multiple light sources, including arrayed LEDs of different colors in various geometries. Currently favored illumination geometry, however, as noted earlier provides a single light source such as an LED 433 (FIG. 10).

Figure 9:
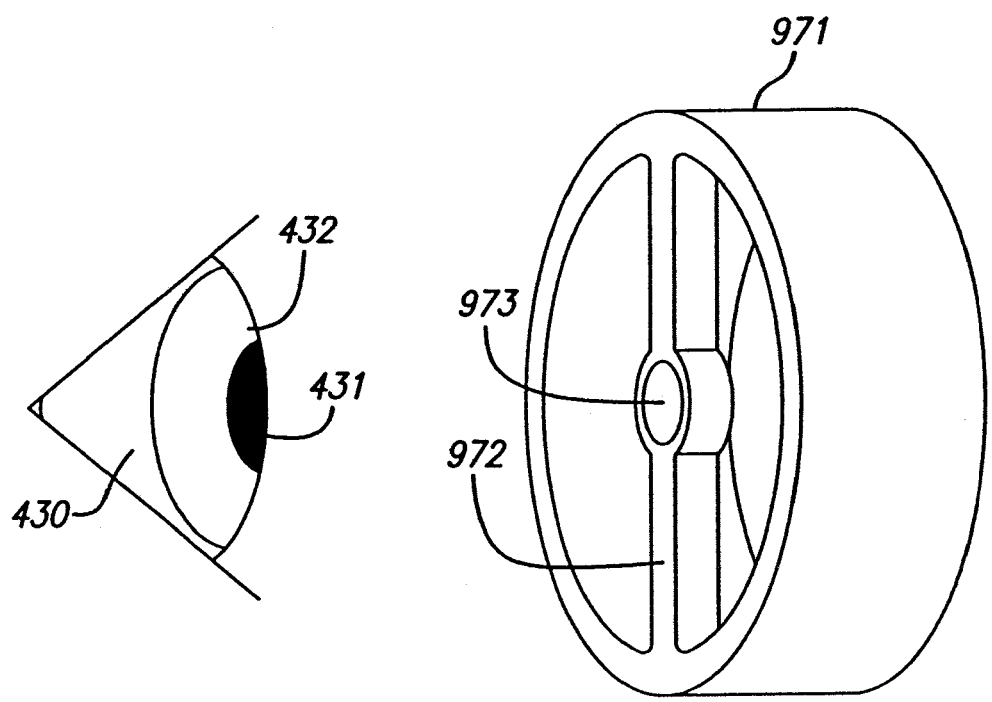
FIG. 9 is a perspective view of an early bezel for mounting at the front of the camera lens and for aiming a small light source toward the eye.

In the best of these configurations, the LED was held centered by a diametral vane or web 972 (FIGS. 9 and 10) with a hollow central hub 973 for the LED, in an aluminum bezel 971. The LED is held in front of the camera lens and aimed at the eye.

The back of the LED is covered with black tape 1081 to shield the lens (surface) 315 so that none of the direct LED light is picked up by the camera. Only the light reflected by the pupil 431 and iris 432 is seen by the camera. This scheme also enables the subject to center the subject's own eye by looking directly into the LED—or a grain-of-wheat size incandescent bulb.

Bezels were made to accommodate two sizes of LED: a so-called "T1" 3 mm and a "T-1¾" (5 mm). The larger LED masks the entire pupil—thereby negating the data that would be gathered for pupil calibration. The data collected is nevertheless very useful in obtaining the correction factor to establish total system linearity.

The bezel portion that goes over the lens shade has a 1.39 inch inside diameter, with a 0.05 inch wall, 0.3 inch deep. The web that holds the LED has a thickness of 0.04 inch (to minimize the masking of data from the iris to the CCD camera) and is 0.125 inch deep.

A goal during data-taking is to illuminate the iris to the point, at least, ½ full well on the total digital number (D/N) possible—or alternatively full well of the CCD camera. Empirical data-collection and—manipulation suggests that ¼ full well may be a minimum needed to provide the amount of data necessary for all manipulation of calibration, subtraction and averaging for an experimental system.

Although the embodiments described above have employed a personal computer (PC) for data manipulation to get a glucose value, the invention contemplates, as a first step toward portability, making a hybrid integrated circuit to replace the PC. It also appears worthwhile to develop a "foolproof" transmitter coded to transmit blood-glucose values directly to a diabetic's insulin pump, as well as calculation of utilization time and amount of insulin. Eventually continuous readings through a convenient means, such as for example eyeglass-mounted sensors, would bring the diabetic and others back to a more-normal life.

C.11 Wavelength Effects

The glucose response has been observed over portions of the visible and near infrared portions of the light spectrum. Peak response appears to be in the yellow and yellow/green and near infrared portion of the spectrum for the algorithm described above.

It is reasonable to generalize the foregoing observations to note what is common to both wavelength regions—i.e. that the level response is substantially monotonic, namely either an increasing function or a decreasing function for the different wavelength regions respectively.

In one embodiment, a black-and-white CCD array is able to collect sufficient information for blood-glucose determination—reflected light level being distinctly correlated with glucose concentration.

This is accomplished through heavy reliance upon further software manipulation of the data. Such operation is mechanically and optically simpler than, and is to be distinguished from, the measurement mode that is was embodied in earlier prototypes of the apparatus, which employed rotating filter wheels to perform rudimentary spectral differentiation. See referenced United States Provisional Patent Application 60/100,804, "BLOOD SUGAR MEASUREMENT THROUGH THE EYEBALL", filed on Sep. 18, 1998, by Walter K. Proniewicz and Dale E. Winther, which is incorporated by reference herein.

C.12 Image-processing Software

Two programs, "Glucon™" and "Average", were written for implementation of the present invention and were instrumental in performing research and obtaining quantitative results from experimentation. Both programs were developed using a graphical programming language from National Instruments Corporation known as "G™", and also known as LabView™ 5.0—with the IMAQ™ imaging tools. The description above, including the pseudo-code describes the processing of these programs.

The first program, Glucon, extracts information from light wages. It embodies all necessary techniques for obtaining IDN or GLU values. The second program, Average, is used to correlate the IDN or GLU values obtained from an imaged eve with the actual concentration of patient blood glucose. It processes a user-selectable number of images of a subject eye, all taken at a particular glucose level, i.e. in quick succession. In operation, Average creates a statistical box and then obtains the average and absolute IDN or GLU limits. These values are used to build a table of IDN-to-blood-glucose conversions.

Figure 11:
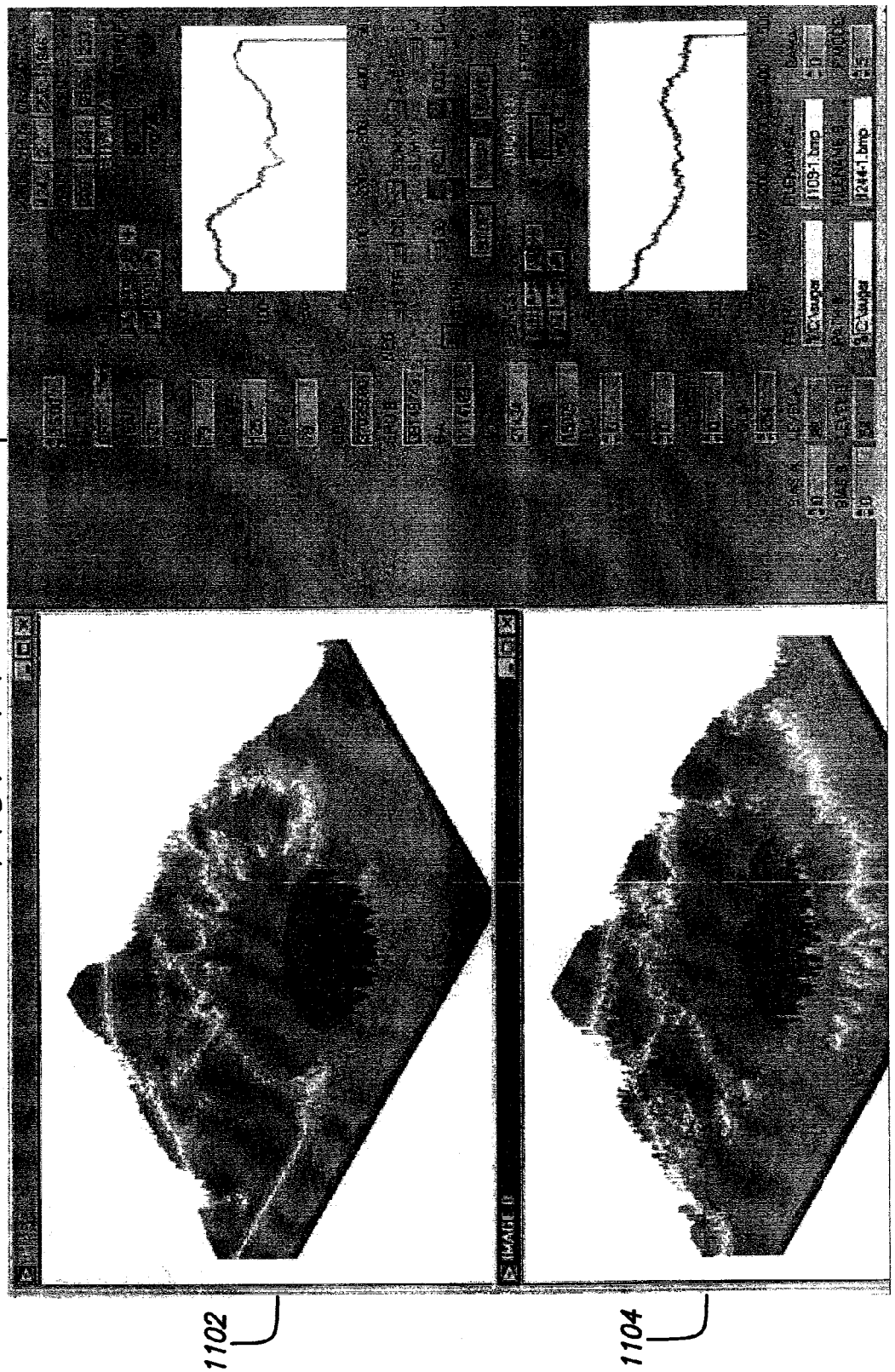
FIG. 11 is an illustration of part of a representative control panel, seen on a computer screen while the system is imaging a subject eye and showing false light images.

FIG. 11 illustrates a control panel 1100. While the noninvasive measurement system is imaging a subject eye with the camera, the noninvasive measurement system displays a control panel on the computer screen that includes various buttons and other controls along with two images (Image A 1102 and Image B 1104). Image A and Image B are two separate images of the same eye, taken at different times, that may be displayed together for comparison. However, the noninvasive measurement system can also display just one of the images. Image A and Image B are displayed by the noninvasive measuring system as false color intensity maps. These images, however, are in black and white format in the attached figures. The center of an image is the pupil and is masked (i.e., zeroed out, which corresponds to a black color). Around the pupil, the dark color is actually red and indicates that the concentration of blood glucose in the eye is high. The GLU or IDN values in milligrams per deciliter (mg/dl) are calculated from the images. Image A and Image B are provided for ease of understanding of the invention, but they are not required to practice the invention.

The control panel 1100 includes an X control that enables setting a filter factor. The Filter control turns a filter on or off. The Mean A control provides the mean of Image A. The DEV A control displays the standard deviation for Image A. The Mean B control displays the mean of Image B. The DEV B control displays the standard deviation of Image B. The GRU A control displays the GRU value for Image A, and the GRU B control displays the GRU value for Image B. The BLK A&B controls display the number of dark pixels (0DN) in the A&B images, respectively. The LO control sets a minimum stretch limit. The HI control sets a maximum stretch limit. The THRESH control sets a threshold, so that when the IDN is being summed up, if the threshold is set, the summing begins at that level but does not include any pixels below that level. The GLIM control indicates that the IDN summation will not include values above this. The BIAS A control adds to the average level of brightness of the pupil for Image A. The BIAS B control adds to the average level of brightness of the pupil for image B. The LEVEL A&B controls indicate the average brightness of the pupil for each image. The PATH A and FILENAME A provide the path and filename used to locate the storage location of Image A. The PATH B and FILENAME B provide the path and filename used to locate the storage location of Image B. The GAMA control is a gamma stretch control. The F MODE control select the different filter shape modes.

The XPOS control provides a readout of the X position of the mouse on an image, and the YPOS control provides a readout of the Y position of the cursor on an image. Together, the XPOS and YPOS enable selection of a particular pixel. The DN control displays the data number of the pixel located under the cursor. The DELTA control shows the difference between the line or row image segment sums between the A and B frame. These are the cumulative values of the pixels shown in the 2 waveform charts shown in FIG. 11. The Switch marked SUM X/SUM Y selects between row and columns in the image and these data are summed. The sums are compared and displayed by the DELTA control. The CENT A&B controls indicate the X and Y position of the centroid of the respective image. The A&B LINES control permits user manipulation of the SUM charts in FIG. 11. The SUGAR A control displays the glucose level that correlates to Image A. The ERROR A control is lit when an error is detected. When the ERROR A control is lit, the SUGAR display is blanked out. The NEG control is red when the second frame (i.e., image B) has a smaller GRU that of the first frame (i.e., Image A). It is green when the second frame has a larger GRU than that of the first frame. The STR control turns on a primary linear stretch. The COL control allows selecting false color or black and white, the SUM X and SUM Y control enables showing the sum of X or the sum of Y in the graphs for the two images. The A+B control indicates that two channels (i.e., two images) are being processed. The BW control enables setting the background of the graph to be black or white. The CLONE control enables cloning the second frame into the first frame. Then, if desired, a new frame can be brought into the second frame, to continue comparisons between different frames. The 3D control indicates whether the images are to be show as pseudo 3D. The PCUT control sets the pupil cutter to on or off. The ICUT control sets the IRIS cutter (leaving only the pupil) to on or off. The CAL control is set to on for calibration of the pupil for a linear stretch. The STOP control stops the program. At this time, the picture may be manipulated (e.g., moved horizontally or vertically and the mouse can be used to move the cursor about to identify individual pixel values). The SNAP control invokes a program to snap a picture of the screen and store it as a bitmap. The SAVE button directly saves the picture as a bitmap. The SUGAR B control displays the glucose level that correlates to Image B. The Error B control is lit when an error is detected.

Figure 12:
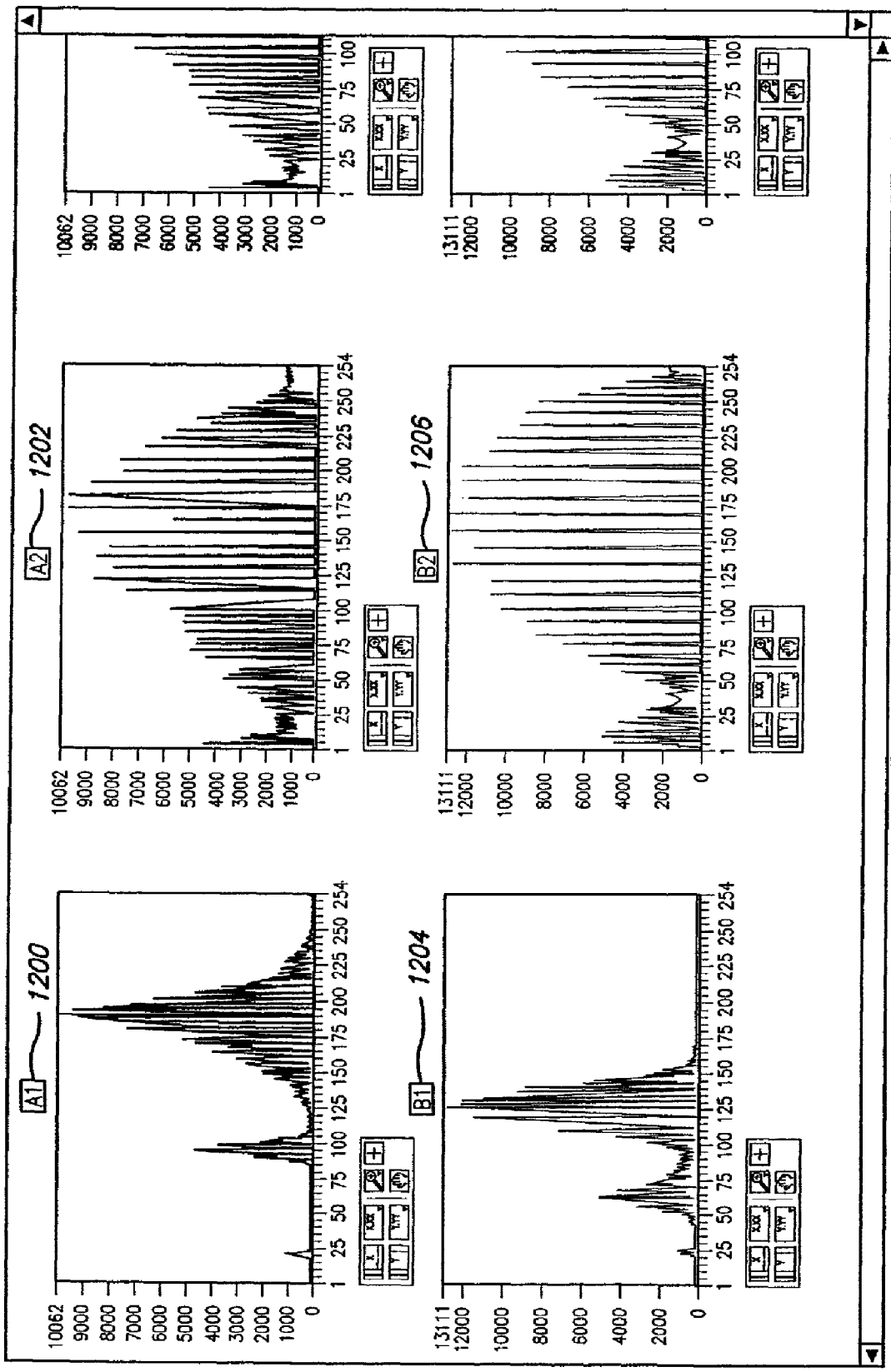
FIG. 12 are representative histograms that are another part of the same control panel display, particularly showing histograms representing results of different processing stages within the program.
Figure 13:
FIG. 13 is a display of a control panel associated with an average program and having controls used to correlate typical values with an actual concentration of patient blood glucose in conventional units.

FIG. 12 are representative histograms that are another part of the same control panel display, particularly showing histograms representing results of different processing stages within the program. Histogram A1 1200 represents Image A (from FIG. 11) initially. Histogram A2 1202 represents Image A after data was normalized and stretched. Similarly, Histogram B1 1204 represents Image B (from FIG. 11) initially. Histogram B2 represents Image B after data was normalized and stretched FIG. 13 is a display of a control panel associated with an average program and having controls used to correlate typical values with an actual concentration of patient blood glucose in conventional units. The Average program is used by the noninvasive measurement system to obtain calibrated IDN-to-GL data from the IDN values. The COUNT control selects the number of image frames to be processed in the calibration average. The AVNUM control is the average GRU obtained from the selected frames. The AVPIX control is the average pixel brightness for all of the input images in the GRU average. The PATH and FILENAME controls display the path and file name of the last image being processed. The AVMIN control is the minimum average GRU from all of the processed images. The AVMAX control is the maximum average GRU from all of the processed images. The +DELTA control indicates the GRU error delta from the average GRU in the positive direction. The −DELTA control indicates the GRU error delta from the average GRU in the negative direction. The +PRCNT control indicates the maximum GRU error percentage above the average. The −PRCNT control indicates the minimum GRU error percentage below the average. The CAL control enables the pupil calibration to be applied to the Automatic Stretch algorithm. The PCUT control sets the pupil cutter to on or off. The GLIM control indicates that the IDN summation will not include values above this. The LEVEL control indicates the average pupil brightness.

C.13 Glaucoma Measurements

The noninvasive measurement system also uses the curvature of the iris to obtain glaucoma pressure at close focal length. An eye machine can be used to automatically give a difference in comparative focal lengths of inner iris vs. outer iris as an indicator of pressure.

Figure 14:
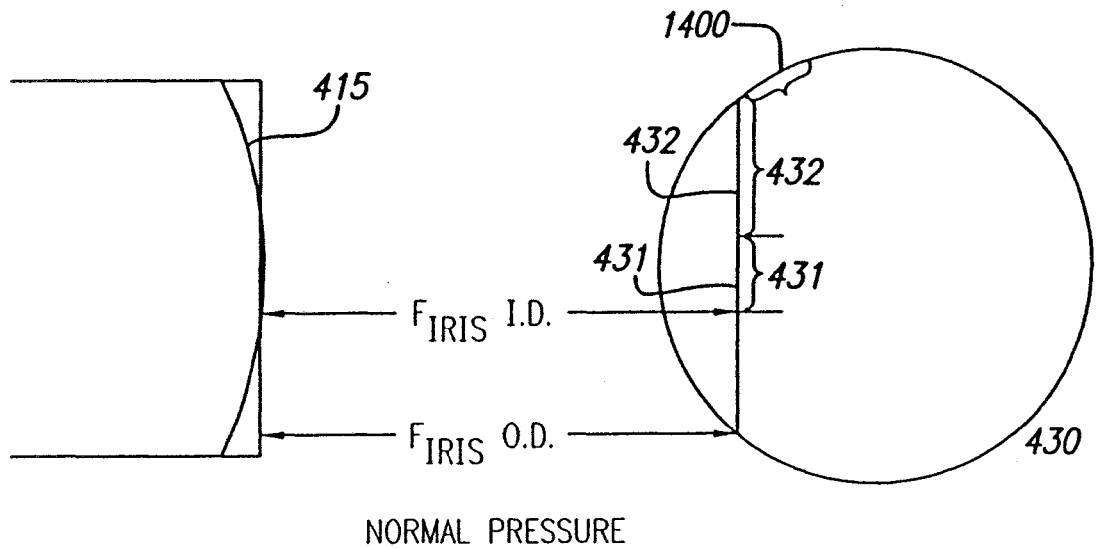
FIG. 14 is a diagrammatic showing of focal-distance measurements that can be used to determine glaucoma pressure automatically with apparatus analogous to certain forms of the glucose-concentration measuring systems described herein.
Figure 14:
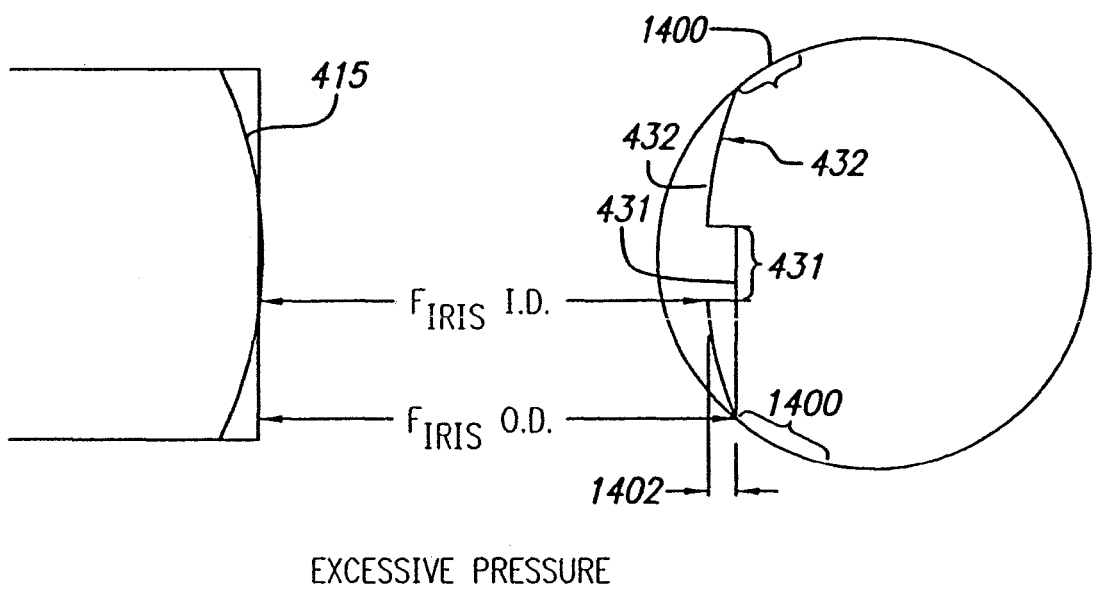

FIG. 14 illustrates the use of the noninvasive measurement system to identify glaucoma pressure. The distance $F_{iris\ ID}$ represents the distance from the vertex plane of a CCD camera lens 315 to the inside diameter (ID) of the iris—in other words, to the circular transition between the iris 432 and the pupil 431. Analogously $F_{iris\ OD}$ represents the distance from the lens vertex plane to the outside diameter (OD) of the iris—i. e., to the circular transition between the iris 432 and the white 1400 of the eye 430.

In the upper "A" view, these two distances $F_{iris\ ID}$ and $F_{iris\ OD}$ are substantially equal, $F_{iris\ ID}=F_{iris\ OD}$. This indicates a balanced or normal pressure condition within the eye. In the lower "B" view, the two distances are no longer equal: specifically, the ID distance now exceeds the OD distance, $F_{iris\ ID}>F_{iris\ OD}$, thereby indicating abnormal, excessive pressure.

The incremental distance 1402, which is to say the difference $F_{iris\ ID}-F_{iris\ OD}$ (or ratio) between the two distances, is related to pressure. Focal determinations thus yield a measure of intraocular pressure, a large distance corresponding to high pressure and a small distance to low pressure. Depth of field, for example 0.3 mm (0.012 inch), may form a limitation on this technique.

C.14 Flow Diagram and Alterative Embodiments

The noninvasive measurement system comprises apparatus and software for noninvasively measuring glucose concentration in blood. To reduce the complexity of the image-input system, software has been developed to optimize camera positioning and illumination consistencies.

Figure 15:
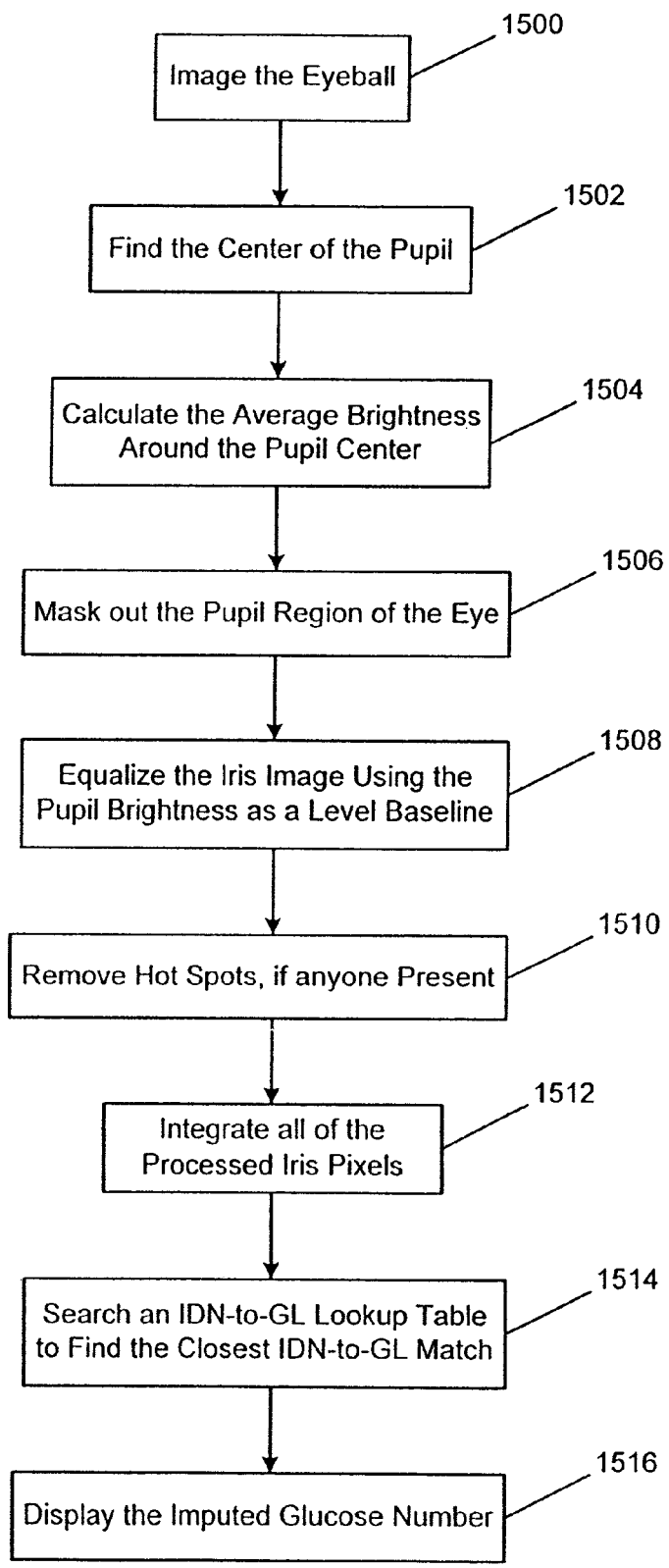
FIG. 15 is a flow diagram illustrating the steps performed by the noninvasive measurement system in one embodiment of the invention.

FIG. 15 is a flow diagram illustrating the steps performed by the noninvasive measurement system in one embodiment of the invention. In block 1500, the noninvasive measurement system images the eyeball. In block 1502, the noninvasive measurement system finds the center of the pupil. In block 1504, the noninvasive measurement system calculates the average brightness around the pupil. In block 1506, the noninvasive measurement system masks out The pupil region of the eye. In block 1508 the noninvasive measurement system equalizes the iris image using the pupil brightness as a level baseline. In block 1510, the noninvasive measurement system removes hot spots, if any are present. In block 1512, the noninvasive measurement system integrates all of the processed iris pixels. In block 1514, the noninvasive measurement system searches a IDN-to-GL lookup table to find the closest IDN-to-GL match. In block 1516, the noninvasive measurement system displays the imputed glucose number.

The noninvasive measurement system has several facets or aspects which are usable independently, although for greatest enjoyment of their benefits they are preferably used together and although some of them do have some elements in common.

In embodiments of a first of its independent aspects, the noninvasive measurement system measures blood-glucose concentration in a biological entity by measuring light reflectivity from the body. The noninvasive measurement system includes a technique for directing light to such body (e.g., a light bulb). In addition the noninvasive measurement system includes a technique for receiving (e.g., with a camera) and processing (e.g., with a computer) light reflected from such body substantially without spectral analysis of the reflected light. The foregoing may represent a description or definition of the first aspect or facet of the invention in its broadest or most general form. Even as couched in these broad terms, however, it can be seen that this facet of the invention importantly advances the art.

In particular, this facet of the invention entirely eliminates need for piercing the body or otherwise obtaining blood samples, and so avoids the discomfort, fear and other detriments discussed above. Furthermore this aspect of the invention is advantageous in that it requires no elaborate spectral modulation, or multiple detectors for different wavelength regions, or dispersive elements—such as required to perform spectral analysis.

The absence of requirement for spectral analysis is a direct result of the discovery that light reflected from the iris bears a monotonic relationship (though different in different wavelength regions) to glucose concentration in the blood.

Although the first major aspect of the invention thus significantly advances the art, nevertheless to optimize enjoyment of its benefits preferably the invention is practiced in conjunction with certain additional features or characteristics. In particular, preferably the technique for directing light to an eve of the body and the technique for receiving and measuring include a technique for receiving and measuring light reflected from the eye.

Further preferably the receiving and measuring a technique comprises a monochrome detector array—and in this case still more preferably the monochrome detector array comprises a black-and-white charge-coupled-detector (CCD) camera or detector. Another related preference is that the receiving and measuring a technique includes a digital processor for analyzing signals from the CCD camera.

More generally, such a processor is desirable for analyzing signals representative of quantities of the reflected light. In this case one preference is that the digital processor be part of a personal computer, and the blood glucose level is reported on a monitor screen of the computer.

An alternative preference, however, is that the noninvasive measurement system be a handheld portable unit, that the unit include a technique for reporting for indicating the blood glucose level, and that the digital processor be part of the handheld portable unit. In this case preferably the reporting technique includes an LCD unit for visually indicating the blood glucose level.

Another basic preference is that the receiving and measuring technique includes a technique for detecting change in level of the reflected light, and relating said change to blood-glucose concentration. Still another is that the receiving and measuring technique include some technique for detecting change in level of the reflected light—and also some technique for reporting glucose concentration that varies substantially monotonically with reflected-light level. Another general preference is that the detecting technique include some technique for responding to reflected visible light and, in this case, particularly to light in the yellow, yellow-green and infrared portions of the spectrum.

Although the noninvasive measurement system has been described as operating substantially without spectral analysis, this is not intended to imply that the noninvasive measurement system is necessarily entirely unable to differentiate between spectral regions. For instance, preferably the noninvasive measurement system includes a technique for eliminating response to some particular light band—e.g. the red or infrared, or both. Similarly the technique for receiving and measuring substantially without spectral analysis preferably do take into account different signal responses in the red or infrared as opposed to the yellow/yellow green portion of the spectrum.

In embodiments of a second major independent facet or aspect, the noninvasive measurement system measures blood-glucose concentration in a biological entity by measuring light reflectivity from the body. The noninvasive measurement system includes a self-contained case. It also includes a technique for directing light to the body. Also included is a technique for receiving and measuring light that is reflected from the body. The foregoing may represent a description or definition of the second aspect or facet of the invention in its broadest or most general form. Even as couched in these broad terms, however, it can be seen that this facet of the invention importantly advances the art.

In particular, because it has been established through experimentation and testing that the entire invention is capable of reduction to be carried within a self-contained case, the many benefits of noninvasive measurement can be enjoyed in a unit that need not take the form of a machine only suited for use in a medical facility. Rather, the invention can be implemented in a machine suited for patients' use at home, or at an ordinary office or other business—or in cars, restaurants, etc.

Although the second major aspect of the invention provides significant advantageous features, nevertheless to better optimize enjoyment of its benefits preferably the invention is practiced in conjunction with certain additional features or characteristics, in particular, preferably the case is fully portable. Also in this instance preferably the case fits in the palm of a normal-size adult's hand.

In embodiments of a third of its major independent facets or aspects, the noninvasive measurement system measures blood-glucose concentration in a biological entity by measuring light reflectivity from an eye of the body. The noninvasive measurement system includes a technique for directing light to an iris of such eye. It also includes a technique for receiving and measuring light reflected from such iris. Also included is a programmed digital processor that analyzes the measured reflected radiation and computing blood glucose concentration therefrom—and in particular uses a reflection of the light source, from the eye, as a peak amplitude point for image alignment. The foregoing may represent a description or definition of the third aspect or facet of the invention in its broadest or most general form. Even as couched in these broad terms, however, it can be seen that this facet of the invention provides importantly advantageous features.

In particular, the eye is generally available for optoelectronic measurements without the subject's disrobing or any other great inconvenience. Moreover, condition of the blood in the eye is generally particularly rapid in its response to or tracking of the condition of the blood in other critical parts of the body particularly the brain.

Although the third major aspect of the invention provides significant advantageous features, nevertheless to better optimize enjoyment of its benefits preferably the invention is practiced in conjunction with certain additional features or characteristics. In particular, preferably the receiving and measuring technique also includes a technique for receiving and measuring light from a pupil of the eye. This preference facilitates determination of a baseline dark level, or of an illumination level provided by the light directing technique, or both.

In embodiments of a fourth of its major independent facets or aspects, the noninvasive measurement system is a blood-glucose measuring technique. The technique includes the step of imaging forward surfaces of a person's eye on an electronic camera. It also includes digitizing resultant image signals from the camera. Further the technique includes processing pixel signals representing the iris, separately from pixel signals representing other parts of the eye, to determine blood-glucose level. The foregoing may represent a description or definition of the fourth aspect or facet of the invention in its broadest or most general form. Even as couched in these broad terms, however, it can be seen that this facet of the invention importantly advances the art.

In particular, analysis of conditions in the iris is advantageous in that the iris exhibits monotonic relationships (peculiar to different wavelength regions) between reflected light level and glucose concentration, enabling enjoyment of the previously mentioned benefits of measurement without spectral analysis.

Furthermore the separation of iris and pupil signals for processing is amenable to straightforward implementation based upon geometry, leading to easy compensation for varying illumination level and the like as previously mentioned.

Although the fourth major aspect of the invention thus significantly advances the art, nevertheless to optimize enjoyment of its benefits preferably the invention is practiced in conjunction with certain additional features or characteristics. In particular, preferably the technique also includes the steps of processing pixel signals representing the pupil to obtain a baseline dark level or an illumination level, or both—and also applying the dark level or illumination level, or both, to refine the pixel signals representing the iris. In this case advantageously the processing step includes applying an average reflected intensity level of the pupil to represent the dark level baseline.

Another general preference is that the iris-pixel signal processing comprises integrating all usable iris-pixel signals to produce a unitary intensity indication, in this case preferably the applying step includes integrating into the indication only—intensities that are higher than that of the pupil.

Yet another basic preference is to include the step of substantially removing image scene and illumination variation. Still another preference is to include the step of calibrating readings for an individual patient.

Another general preference is to include masking out the pupil pixels from the iris region. In this case the masking step also preferably includes applying a software pupil mask that substantially stabilizes the number of iris pixels available for use, and substantially stabilizes pupil centering within the iris image. Further if this is done preferably also the pupil mask is larger than the largest pupil diameter occurring in measurement conditions.

Other general preferences relative to the technique of the invention include these steps, considered individually:
  masking out the pupil pixels from the iris region;
  diffusing source light to minimize hot spots;
  removing peak signal amplitudes, to minimize the effect of illumination hot spots;
  mapping illumination hot spots, to enable disregarding 5 hot-spot regions in said processing step;
  adjusting image contrast to substantially fill the complete dynamic range of pixel data words;
  looking up the measured level in a lookup table to obtain a corresponding numerical blood-glucose concentration indication in quantity of glucose per unit blood volume; and
  said digitizing step comprises distinguishing very low light-intensity changes.

Another preference, still as to the fourth aspect of the invention, is this sequence of steps:
  finding a center of the pupil of the eye; calculating average brightness around a pupil center;
  masking out the pupil region of the eye;
  a equalizing the iris image using the pupil brightness as a level baseline;
  removing hot spots if present;
  integrating all of the processed iris pixels to obtain a numerical representation of brightness level of the iris;

searching a lookup table to apply a previously developed calibration and thereby determine an imputed glucose concentration in quantity of glucose per unit volume; and displaying the imputed glucose concentration.

In embodiments of a fifth major independent facet or aspect, the noninvasive measurement system is a blood-glucose measuring technique for use with a small light source. This technique includes the step of automatically finding a reflection, from a patient's pupil, of the light. The technique also includes the step of automatically performing a position alignment based upon the location of the reflection of the light. The foregoing may represent a description or definition of the fifth aspect or facet of the invention in its broadest or most general form. Even as couched in these broad terms, however, it can be seen that this facet of the invention importantly advances the art.

In particular, this mode of operation very easily resolves several otherwise knotty problems of alignment, which can otherwise threaten the integrity of the overall measurement process—since the process is sensitive to alignment and control of signal returns from the white of the eye as well as the pupil.

Although the fifth major aspect of the invention thus significantly advances the art, nevertheless to optimize enjoyment of its benefits preferably the invention is practiced in conjunction with certain additional features or characteristics. In particular, preferably the technique also includes zeroing-out the area within the light source, to form an image of forward surfaces of the eye without the light source.

Another preference, especially when the technique is for use with a centrally disposed light source, is the step of growing a pupil mask—starting from the light source as a centerpoint—to cover the pupil area in the image. In this case, preferably the technique also includes capturing brightness level in an area under the aligned pupil mask, for use in a dark-level calibration.

In embodiments of a sixth major independent facet or aspect, the noninvasive measurement system measures blood glucose concentration in a biological entity by measuring light reflectivity from an eye of the body. This noninvasive measurement system includes a detector array. It also includes a small light source held-directly in front of the detector array, for directing light to the eye. In addition the noninvasive measurement system has a technique for receiving and measuring light reflected from the eye. The foregoing may represent a description or definition of the sixth aspect or facet of the invention in its broadest or most general form. Even as couched in these broad terms, however, it can be seen that this facet of the invention importantly advances the art. In particular, use of a source in the described position greatly simplifies, in several ways, the processing of data derived from the optical system.

Although the sixth major aspect of the invention thus significantly advances the art, nevertheless to optimize enjoyment of its benefits preferably the invention is practiced in conjunction with certain additional features or characteristics. In particular, preferably the noninvasive measurement system also includes a lens between the detector array and the light source.

In this case, it is that the light source shine toward the eye from substantially the geometric center of the lens—or, alternatively of the detector array. In this case the noninvasive measurement system further includes a technique for using a reflection of the electromagnetic-radiation source, from the eye, as a peak amplitude point for finding the image center.

A more general preference, still as to this sixth main aspect of the invention—and especially when the noninvasive measurement system is for use in measuring blood-glucose concentration for the body of a human being—is that the light source serve as a visual centering target for the human being. In such a system, the human being looks substantially directly toward the light source to, in substance, automatically align or center (at least approximately) the pupil in the optical field.

In embodiments of a seventh major independent facet or aspect, the noninvasive measurement system measures blood glucose concentration in a biological entity, by measuring light reflectivity from blood of the body. The noninvasive measurement system includes a technique for directing light to the blood. It also includes a technique for receiving and measuring light reflected from the blood substantially without spectral analysis of the reflected light.

From all the discussion, in this document, of aspects of the invention, those skilled in the art will understand that the invention operates, in one way or another, based upon presence of the blood in the iris or elsewhere within the body—thereby making the blood available for optoelectronic measurement. Accordingly the invention is not limited to the implementations expressly set forth.

D. Noninvasive Measurement of Glucose Concentration in an Eye Using a Phase Angle and Amplitude Light is an electromagnetic wave. A wave has an amplitude, which is its positive or negative displacement from an equilibrium point. A glucose molecule rotates in a clock-wise direction as its density increases. (On the other hand, a fructose molecule rotates in a counter-clockwise direction, and the noninvasive measurement system can distinguish between these molecules based on their rotation.) This clockwise rotation affects the polarization. In one embodiment, the invention takes into account that rotation affects polarization. The more glucose there is in the blood, the more light that is reflected. In particular, with polarization, there is a flash of reflected light (as reflective portion of glucose is struck by light), then no reflection (as glucose rotates such that the light strikes, for example, blood, which absorbs the light), another flash of reflected light, etc. The light that is reflecting at different angles appears to be rotating, therefore, the amplitude changes.

A CCD is a charge coupled device whose semiconductors are connected so that the output of one is the input to another. A CCD camera is based on electronic chips called CCD sensors. These components are sensitive to light and allow pictures to be stored in computers. A CCD chip is an array of light-sensitive regions called wells. The wells are charged by the electrons generated by the light. Each light element that reaches the CCD array displaces some electrons that are providing a current source. The current sources are localized in small delimited areas called pixels. The pixels form a CCD matrix.

In particular, the surface layer of this chip contains a grid, and each cell of the grid is a silicon diode which builds an electrical charge proportional to intensity and time light falls on it. A discharging circuit is connected to all cells. Behind these cells is a matching grid of pixels (i.e., a CCD matrix). Each cell stores an analog voltage rather than an off-on (binary) value. The storage capacity of a pixel is also referred to as a well, and the electric charge storage capacity of a typical pixel can hundreds-of-thousands of electrons.

The charges are converted to voltages that can be interpreted by an analog to digital (A/D) converter. In the A/D converter, the electric charge of a pixel is converted to an 8-bit number ranging from 0-255. The 8-bit number is referred to as a pixel data number. The pixel data number represents the converted amplitude of each pixel. In an alternative embodiment, the pixel data number may be "stretched". That is, if the pixel data number is 16, the numbers 0-16 may be mapped to 0-255, so that the stretched pixel data number is 255 (i.e., 16 may be mapped to 255). Of course, one skilled in the art would recognize that other mapping mechanisms may be used (e.g., mapping 0-31 to 0-255, with 16 mapping to 127).

The image of the eye is used to form a CCD array, which is also referred to as a CCD matrix. The CCD matrix represents each pixel with an entry in the matrix. Each entry has a value ranging from 0-255. The phase angle is determined from a CCD matrix. The rows of the CCD matrix are summed up, and then these values are totaled to form an XGRU value. The columns of the CCD matrix are summed up, and then these values are totaled to form a YGRU value. The ratio of the XGRU value and the YGRU value results in the phase angle. For example, if the light falls symmetrical, the XGRU value and the YGRU value are the same. However, for a substance, which is non-symmetrical, the XGRU value and the YGRU value are not the same. Additionally, the sum of the XGRU and the YGRU is the amplitude.

The following sample CCD matrix is provided only for illustration. One skilled in the art would recognize that a much larger matrix would in practice be used. Also, to simplify the illustration, each pixel will be set to one of three states: 0, 1, 2. Of course a pixel can be of 0-255 states for an 8-bit system, and a pixel can have greater resolution with a larger bit system. The following is a sample CCD matrix:

| 0 | 1 | 2 | 0 | 3 |
|---|---|---|---|---|
| 2 | 2 | 1 | 0 | 5 |
| 1 | 2 | 1 | 1 | 5 |
| 1 | 0 | 0 | 1 | 1 |
| 4 | 5 | 4 | 2 |   |

The noninvasive measurement system obtains row information YPA (summation of rows) and column information YPB (summation of columns) and calculates a true phase angle and a true GRU/true amplitude with the following:

$$\text{true phase angle} = \frac{YPA - (YPA - YPB)}{YPB - (YPB - YPA)} \times 10 \text{ MILLION}$$

true GRU/true amplitude GRU=(YPA+YPB).

For example, using the above matrix, the summation of the rows is (3+5+5+1)=14=YPA. The summation of the columns is (4+5+4+2)=15=YPB. The true phase angle is equal to approximately 10714285. The true amplitude is equal to GRU=(YPA+YPB), which calculates the amplitude by removing the phase angle. Note that the true amplitude GRU is calculated by summing all of the pixels when the matrix is at 680×480, while YPA and YPB are calculated for a reduced size matrix of, for example, 380×380.

The noninvasive measurement system uses a Phase/Amplitude lookup table. The Phase/Amplitude lookup table has columns for a frame cousin number (FRC), a glucose level (GL), an amplitude (AMPL), and a phase angle (PHASE). The Phase/Amplitude lookup table was created experimentally. In particular, the Phase/Amplitude table was created by experimenting on an individual, Walter K. Proniewicz. Each experiment consisted of using a camera to obtain an image of an eye of the individual, calculating a GL value for the individual, and calculating a phase angle and amplitude. Traditional (one-touch) glucose monitors were used to verify the validity of the glucose concentration found via the technique of this invention. The Phase/Amplitude lookup table was built by identifying, by this experimentation. GL values that correlated to a phase angle and amplitude pair.

Additionally, the noninvasive measurement system uses a Cousins table. The cousins table has a column for a FRC number (frame cousin), a glucose level (MG/DL), an amplitude (AMPL), a phase angle (PHASE), and columns for eight cousins. One skilled in the art would recognize that the table could have other columns, for example, additional columns for more than eight cousins. The cousins represent nodes that have similar phase angle and amplitude values. The NODE TABLE DATA graph is a graph of phase angle versus amplitude. The top most line in the graph plots the ratio of phase angle to amplitude. The cousin nodes in the Cousin table are nodes that are at approximately the same horizontal axis on the plot of the ratio. For example, for FRC 10, the cousins are FRC 25, FRC 28, FRC 23, FRC 29, and FRC 18. Each of these frame cousins has a similar phase angle to amplitude ratio.

D.1 Overview of Processing

One embodiment of the invention uses the phase angle and amplitude to identify a blood glucose level. This section provides an overview of the processing steps for this embodiment of the invention, along with pseudo-code. Only some of the processing steps will be discussed here to enable the reader to have a better understanding of these steps prior to providing the pseudo-code. Generally, when a Phase/Amplitude Lookup Table is used, the noninvasive measurement system performs the following steps:

1. image the eyeball, with center brightness
2. apply a spatial filter
3. perform automatic level control
4. find a true GRU
5. automatic fine tuning
6. display the identified glucose number The picture may be taken with a black and white video or electronic still frame camera. In an alternative embodiment, a color camera or custom CCD may be used. In yet other embodiments, other detectors, such as quantum well infrared arrays or mercad telluride arrays or specialized radio receivers can be used.

In one embodiment, a calibration mask is used. The calibration mask is placed between the eye and the lens of the camera. For example, one calibration mask may be a circular piece of glass. Imagine a square whose corners touch the circle is drawn on the circle, then, reflective strips of the material to be analyzed (e.g., glucose) are placed between the edge of the square and the edge of the circle, in vertical lines, with one endpoint of the strip touching the square and the other endpoint of the strip touching the circle. The material to be analyzed may be placed on a mask and then sealed. The mask is placed so that the lens system and CCD can see the mask and so that the mask is illuminated by the light source.

The reflective strips have known phase angle and amplitude values. Each strip has different phase angle and amplitude value. For example, each may represent 5 mg/dl increments starting with 35 mg/d. A strip may be the size, for example, of 50 pixels. The number of strips used is the size of the strip divided by the number of pixels to be covered. The comparison will assist in increasing the accuracy of calculating the glucose level. When a picture is taken of the eye, the calculated phase angle and amplitude values may be compared to those of the strips. In particular, the strips will give amplitude and phase angles for very low glucose values, thereby making extremely low glucose readings very accurate. There is visual confirmation of the amount of glucose on the strips, which can be compared to the iris reflections. Both the amplitude and the phase angle are actual (not deduced), thereby eliminating error, and providing quality control, and enabling self checking.

It will be appreciated by those of skill in the art that one can also construct custom silicon arrays (e.g., a CCD) containing optimizing qualities to enhance spectral response for glucose detection. CCDs and custom silicon arrays can be specially processed, modified, or enhanced to heighten their sensitivities to x-rays and other high energy particles. In this case, the noninvasive measurement system may process x-rays or other high energy particles, instead of light waves. Moreover, CCDs and custom silicon arrays can be specially processed, modified, or enhanced to be made sensitive to ultraviolet rays to highlight or detect different types of minerals.

It will be appreciated by those of skill in the art that the noninvasive measurement system may also be used to locate tumors and to locate and correct blood clots. In particular, a photo-multiplier can be placed in front of a CCD to enhance its sensitivity. Then, a high intensity light that is synchronized to the integration time of the CCD is used to send light through an individual. The amount of light in that high intensity light source can penetrate flesh. For example, the noninvasive measurement system may be used to detect breast cancer.

Next, the noninvasive measurement system may apply a spatial filter after taking the picture. The spatial filter, when used in the low-pass mode, reduces unwanted image features that tend to show-up as high frequency components. That is, the spatial filter takes out portions of an image that create "noise" from non-glucose information. The filter parameters used operates on a 3×3 pixel area. The filter will take a group of pixels (e.g., 9 pixels), average the values of the pixels, and set the values of each of the pixels in the group to that value. For example, if 2 of the 9 pixels are lit (i.e., set to one), and the remaining 7 pixels are not lit (i.e., set to zero), the average is zero and all of the 9 pixels are set to zero. For example, tissue in the eye may show up as high frequency, so the low pass filter will remove these components from the image array. A high pass filter will exaggerate these components in the image array. The "hi-passed" data can be processed to uniquely identify an individual person. This can be used as an "iris fingerprint" to identify individuals by the unique characteristics of their iris. The individual eye images can thus be automatically correlated to specific patients.

The noninvasive measurement system may then perform automatic level control. Automatic level control attempts to ensure that the average of all of the pixels is equivalent to the average of a calibrated average (i.e., an average that correlates to the calibrated data or desired average). In one embodiment, the value 35 was found by experimentation to be the best value.

The camera and A/D converter returns the proper amplitudes for glucose detection around this average. The number will be different for other cameras and converters. For example, if the data number is 35, then the automatic level control will find the average of the pixels. If the average is lower than the average data number (e.g., 35), the automatic level control adds 1 to each pixel. If the average is higher than the data number (e.g., 35), the automatic level control subtracts 1 from each pixel. After the addition or subtraction process, the automatic level control finds a new average. If the new average is at or about 35, the automatic level control is complete. Otherwise, the automatic level control continues to add or subtract 1 to each pixel and calculating a new average until the new average is at or about 35.

The noninvasive measurement system calculates a true GRU or true amplitude. The true GRU is the amplitude, with the phase angle portion removed. In particular, the noninvasive measurement system calculates the true GRU as The GRU value—phase angle value. As will be discussed below, this amplitude is matched with the amplitude in the Phase/Amplitude lookup table to obtain the closest amplitude.

In one embodiment, if the phase angle (i.e., the XGRU and YGRU ratio) is found to be an exact match a phase angle in the Phase/Amplitude lookup table, the invention selects that phase angle and amplitude, and the corresponding GLU value, without performing automatic fine tuning. If there is no exact match, automatic fine tuning is performed.

In another embodiment, because it is rare to find an exact match, automatic fine tuning is always performed, without the initial check. Automatic fine involves tuning the Image matrix. The invention attempts to get a close match between the phase angle found with the Image matrix and the phase angles available for comparison in the Phase/Amplitude lookup table. For example, if the phase angle is found by the XGRU and YGRU ratio to be 14020000, the invention attempts to fine tune the value to reach either 14017754 (i.e., node 13 in the Phase/Amplitude lookup table) or 14047686 (i.e., node 14 in the Phase/Amplitude lookup table).

The automatic fine tuning uses a Ternary technique. With the Ternary technique, if ¼ is to be added to the image matrix, 1 is added to each fourth pixel. Then, a new phase angle is calculated. This phase angle is recorded. This is done for 18 passes, with an amount being added each of the 18 times (e.g., 0.1 may be added for the first pass, another 0.1 is added for the second pass, etc.). In each of the 18 passes, a value is added to the pixels in the image matrix, then the phase angle is calculated, then a close match is sought in the Phase/Amplitude lookup table. This results in a FRC value that corresponds to the selected entry in the Phase/Amplitude lookup table. Next, the FRC value is used as an index into the Cousins table. Then, a comparison-is made between the phase angle calculated in the pass and the phase angle for each of the cousins and the selected FRC. The FRC whose phase angle is closes to the calculated phase angle is saved in an array, along with phase angle error (MNP) and amplitude error (MNA). This array results in 18 values corresponding to the 18 passes. A mean phase angle is calculated from the 18 recorded values. This is then compared to the Phase/Amplitude lookup table to find a matching phase angle, amplitude, and corresponding GLU. Also, the GLU value is used to index into the Cousins table. The 18 passes are performed for each of four frame cousins (FRCs). The result is four final values and one is selected from these four.

For each of the 18 steps, start with frame cousin (FRC) 13, which has a GLU value of 136. FRC 13 is used because the GLU value 136 is near the middle of the range. Also. FRC 13 has 8 cousins (the most cousins possible in the Cousins table). Then, a comparison is made between the phase angle and the phase angle in the Phase/Amplitude lookup table for each cousin. During the process, one of the cousins is identified as being closest to 136 by the phase angle. This results in 18 values for each cousin within the FRC. Then, the FRC that is most often closest to the image phase angle is chosen. In one embodiment, there are four iterations, one starting with FRC 13, the next with FRC 14, the next with FRC 15, and the last starting with FRC 16. These frame cousins cover many comparisons because of the number of cousins that they have. Of the four results, the closest match to the Phase/Amplitude lookup table is the selected answer. This answer is displayed, for example, on a monitor connected to a computer.

The focus is on the phase angle and not the amplitude because the amplitude is susceptible to environmental factors. Then, the final result is the GLU whose phase angle and amplitude most closely match an entry in the Phase/Amplitude lookup table.

The following pseudo-code reflects the processing performed by the noninvasive measurement system. Some of the steps occur when particular controls are set on a control panel. These controls will be discussed below.

1. image the eyeball, with center brightness
2. adjust geometry of image to 640×480 pixels to match screen size of personal computer (PC)
3. if programmable level bias is set (in the range of 0-255), perform level bias on image
4. if gamma stretch set, perform gamma stretch (i.e., to produce a non-linear stretch) (normally set for eye measurements, and is set for skin measurements)
5. if pre-stretch set, perform first linear stretch
6. create pupil mask in identified shape (i.e., "L" shape or rectangular shape)
7. corner tab cutter (zero out boxes in corners to remove extraneous light, etc.)
8. if first filter set, use programmable low or high pass filter, whichever is selected
9. if set, find center
10. if second filter set, use programmable low or high pass filter, whichever is selected
11. if stretch set, control stretch from front panel (i.e., user interface)
12. if image rotator set (i.e., can be used instead of Ternary technique), rotate image
13. if automatic level control set, perform automatic level control
14. if manual fine tuning set, perform manual fine tuning (i.e., Ternary technique for biasing image)
15. if automatic fine tuning set, perform automatic fine tuning (i.e., Ternary weights are added in here)
16. if bitmap image format set, change format to an x-y image format (i.e., an x-y array), which removes the bitmap header, etc.
17. calculate GRU (i.e., by summing up all x rows and y columns in the CCD array)
18. convert image from 680×480 to 480×480
19. using 380 pixels (avoid using edges as it affects data, with offset 50 pixels in from edge in each axis, leaving a black margin at edge), sum up x axis and y axis and divide largest by smallest to get value that is greater than one
20. obtain row information YPA (summation of rows); column YPB (summation of columns) by calculating the following:

$$\text{true phase angle} = \frac{YPA - (YPA - YPB)}{YPB - (YPB - YPA)} \times 10 \text{ MILLION}$$

true GRU/amplitude=GRU−(YPA+YPB)

Figure 16:
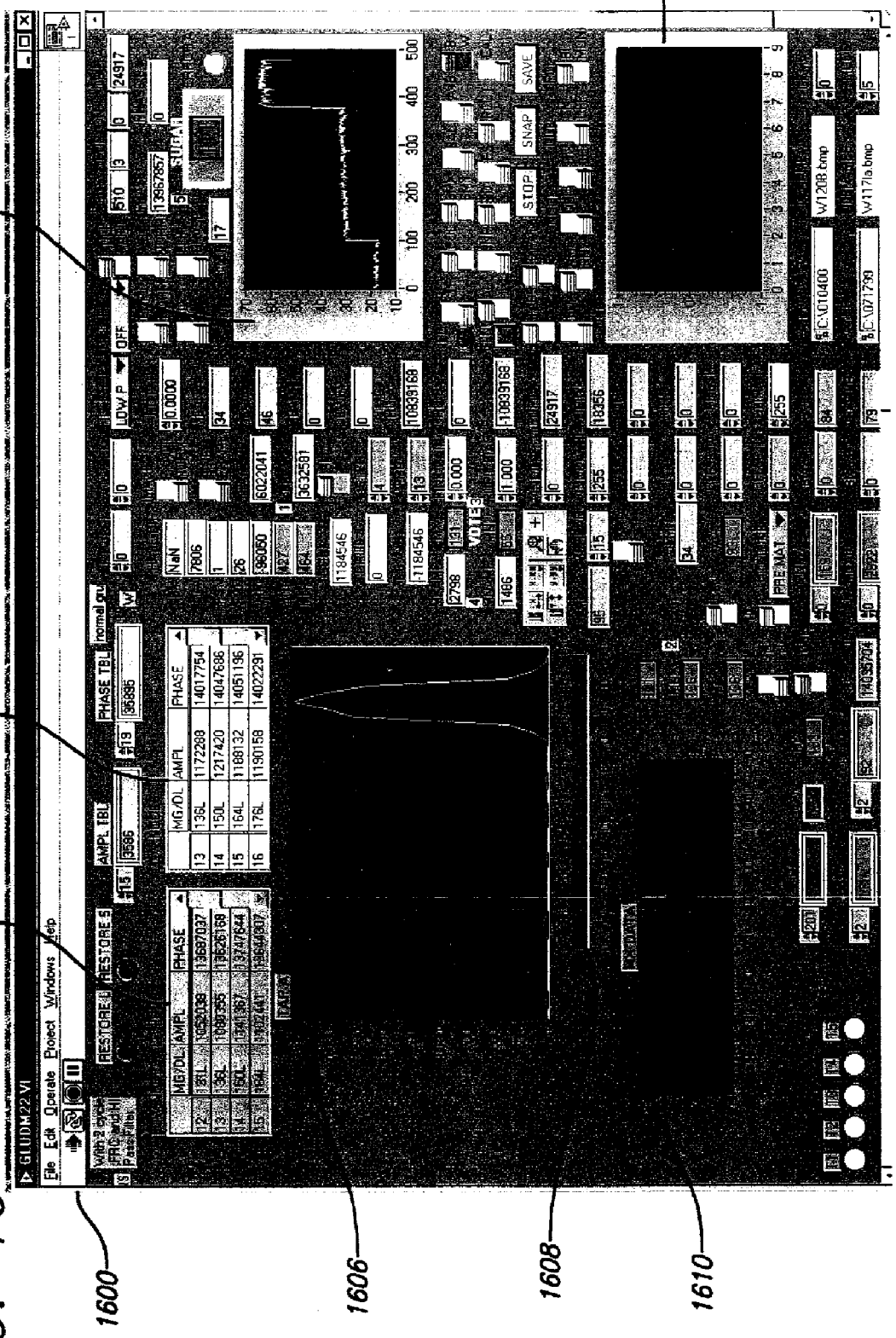
FIG. 16 illustrates a control panel for one embodiment of the invention.

21. perform automatic fine tuning, with 18 passes for each of 4 FRC values
22. select best true phase angle and true amplitude match
23. display results D.2 Controls and Tables FIG. 16 illustrates a control panel 1600 for one embodiment of the invention. The Phase/Amplitude look up tables 1602 and 1604 have been calibrated for different options. The Phase/Amplitude look up tables 1602 is a LOW NODES ALC HP, which means that it was calibrated for low brightness (LOW NODES), using a automatic level control (ALC), and a high pass filter (HP). The Phase/Amplitude look up tables 1604 is LOW NODES, which means that it was calibrated for low brightness (LOW NODES). The RESTORE L control enables restoring a Phase/Amplitude look up table with a large base table. A base table is a Phase/Amplitude table, with large indicating it has the full range of glucose levels and small indicating it does not have the full range of glucose levels. The RESTORE S control enables restoring a Phase/Amplitude look up table with a small base table. The AMPL TBL control displays an index, (e.g., 15), and a value corresponding to that index. The PHASE TBL control displays an index and a value corresponding to that index.

The TAPA histogram 1606 displays the total energy of the incoming source. The bar 1608 indicates the processing of the FRC values. The MX DATA histogram 1610 has an x-axis that goes from 1-450 milligrams and displays a statistical distribution of findings of 1-18 steps. The MXHD control displays the data of an array that holds the 4 FRC values. The PEAK control displays the peak value from the histogram 1610. The RESD control displays the four glucose levels that correspond to the four FRC values selected with the auto fine tuning. The RES control displays the glucose level of the last FRC processed. The AVD control displays the average mg/dl value for each of the 4 FRC steps. The AVX control displays the average amplitude. The MNX control displays the minimum amplitude. The MAX control displays the maximum amplitude. The 2CYL/1CYL control enables switching between 1 or 2 cycles. The PAUSE control enables pausing the processing. The PHASE AT MATCH control displays the phase angle selected by the matching.

The error controls T1-T5 are lit upon the occurrence of certain error conditions. The T1 control is lit when the phase code is too low. The T2 control is lit when AVX and MNX are the same (i.e., these are the average and minimum amplitudes). The T3 control is lit when MX and MN are the same (i.e., these are the minimum and maximum glucose levels that are found). The T4 control is lit when MXAMP and MNAMP are the same. The T5 Control is lit when the phase code is out of bounds.

Moving back to the top of the control panel, the PTWEEK control is a phase tweek that enables forcing the phase angle value to a particular value. The ATWEEK control is an amplitude tweek that enables forcing the amplitude value to a particular value. For a first filter, the FILTER1 control enables setting no filter, a low pass filter, or a high pass filter. For a second filter, the FILTER2 control enables setting no filter, a low pass filter, or a high pass filter. The FULL/PART control selects the portion of the Phase/Amplitude table to be used in the look-up process. FULL permits a look-up from FRC 0-37 and PART permits a look-up from FRC 10-18.

The XPOS control provides a readout of the X position of the mouse on an image, and the YPOS control provides a readout of the Y position of the cursor on an image. Together, the XPOS and YPOS enable selection of a particular pixel. The DN control displays the data number of the pixel located under the cursor. The DELTA control shows the difference between the line or row image segment sums between the A and B frame. These are the cumulative values of the pixels shown in the 2 waveform charts shown in FIG. 11.

The PUPL/NORM control is not used. The A-B/NORM control subtracts two images (e.g., Frame A-Frame B). The SIG Control is an edge detection filter, which is a version of a high-pass filter. The FLIP/PHASE control enables inverting a phase angle. The ITER control displays an iteration of the 18 passes. The PHASE A and PHASE B controls are ratios for two images, Image A and Image B, respectively. The SUGAR control displays a glucose level. The ERROR A control is lit when an error occurs. When the ERROR A control is lit, the SUGAR display is blanked out.

Moving to the graph on the right side, the A LINES graph 1612 displays either the summation of the X values or the summation of the Y values from the CCD matrix, depending on which is selected with the SMX/SMY control, for Image A.

The NEG control is lit red when the second frame (e.g., for Image B) has a smaller GRU than the GRU of the first frame (e.g., for Image A). The STR control turns on a primary linear stretch. The COL control shows false color or black/white for the images that are displayed. The BAL control balances based on the geography of a pupil if there are few iris pixels to work with (e.g., pupil too big). The A/B control enables working with two channels (i.e., two images) at once. The BIW control enables, for all charts, either a black background or a white background.

The CLN Control enables cloning the Image B file name to the Image A file name to speed up manual processing. This avoids manually typing the information. The ALC control sets automatic level control. The INP control displays the input image, rather than a processed image. The 3D control is used to select a 3D display format for false light intensity maps. The PS control is a prestretch (before any other processing occurs). The PCUT control sets a pupil cutter. The CAL control is on for calibration of a pupil for a linear stretch.

The TABS control sets 4 corner tab masks. The LPAT control enables selecting a square or L-shaped mask for the pupil. The BOX control is used to box in part of an image. The AMP/PHS control is used to select either amplitude or phase angle for indexing into the Phase/Amplitude table when a best possible match is being sought. The STOP control stops the program. The SNAP control invokes another program to snap a picture of the screen and store it as a bitmap. The SAVE control directly saves the image displayed as a bitmap. The NODES DBL control can change the HI/LOW control, which selects a high brightness or low brightness Phase/Amplitude lookup table, to select two other tables. The DLTA control causes comparisons to be made where the final result is selected based on the same comparison polarity. If the incoming phase angle is higher than the nearest table entry and the amplitude is lower than it's table entry, the comparison will be rejected. The POL control is for polarity. In particular, during comparison of values in the Phase/Amplitude lookup table, if BI is set, the answer can be above or below the actual value, and if MON is set, the value is the lower value found. The B LINES graph 1614 displays either the summation of the X values or the summation of the Y values from the image matrix, depending on which is selected with The SMX/SMY control, for Image B.

The PATH A and FILENAME A provide the path and filename used to locate the storage location of Image A. The PATH B and FILENAME B provide the path and filename used to locate the storage location of Image B. The GAMA control is a gamma stretch control. The F MODE control enables manipulating the filter scope mode.

Moving back to the center of the control panel, there are several PHASE DIF controls. The B-A control is the phase angle difference between the A and B image channels. The T-A control shows the difference between the incoming phase angle and the table phase angle as indexed by the current amplitude match. The PPSN control show the best FRC match based on the best phase angle match found during a cousin table scan. The APSN control shows the best FRC match based on the best amplitude match found during a cousin table scan. The AMPL control shows the difference between the incoming amplitude and the table amplitude as indexed by the current amplitude match. The MNP control displays the phase angle error. The MNA control displays the amplitude error.

The TGRUA control displays the true GRU for Image A. The TGRUB control displays the true GRU for Image B. The T B-A control displays the difference in true GRU between the A and B image channels. The MXAMP control displays the maximum amplitude, the MNAMP control displays the minimum amplitude. The MX control shows the maximum GLU value. The MN control shows the minimum GLU value. The UFM control displays the average before a filter is applied. The ERD control, is set, will set the ERROR A control if any error indicator T1-T5 are on. The PUFMI control displays the average before ALC is applied. The AV control displays the average of MX and MN. The CSN control indicates whether the CSN table (i.e., the cousins table) should be used or the primary FRC value should be used for comparisons. The 10X control indicates how much should be added to the CCD array in each of the 18 passes. The AUTO TUNE control allows for selecting either pre-matrix (i.e., a sweep of amplitude before decoding phase angle and amplitude) or post-matrix (i.e., a sweep of amplitude after decoding phase angle and amplitude). The MNPD control holds the MNP values. The MNAD control holds the MNA values.

Moving back to the top, the IMAGE control enables using the input picture exactly as it is or normalizing the picture to be 480×680. The LINE/FRAME control enables capturing a line or a frame. The YPA control displays the XGRU. The YPB control displays the YGRU. The SEQ control enables selection of the number of FRC values to process with 18 passes, and this can range from 0-37. The FRC control enables selection of the FRC value to start with. The FINE GAIN control is manual fine tuning, which forces an offset with a Tenary gain. The PUPIL BIAS control is a pupil size compensator. The WINDOW LO and WINDOW HI controls enable selection of a low and high value, respectively, between 0-255; the result of this is that specific pixels in the range are selected for processing.

The LOS control sets a low limit on a secondary stretch, and the HIS control sets a high limit on a secondary stretch. The LOP control sets a low limit on a primary stretch, and the HIP control sets a high limit on the primary stretch. The OFFSET A control puts a numerical offset to the entire Image A, the OFFSET B control puts a numerical offset to the entire Image B. The BIAS A control enables adding to the computed pupil average of Image A. and the BIAS B control enables adding to the pupil average of Image B.

The ROT control is used to rotate the image. The MEAN A control displays the mean of Image A, while the DEV A control displays the standard deviation. The MEAN B control displays the mean of Image B, while the DEV B control displays the standard deviation. The GRU A control displays the GRU of Image A, while the GRU B control displays the GRU for Image B. The B-A control the raw GRU difference between image A and image B. The PUPIL A control displays the brightness (before average) of the pupil of Image A. The PUPIL B control displays the brightness (before average) of the pupil of Image B. The threshold control indicates at what value the GRU should be summed to. The GLIM control indicates at what value the system should not sum after. The LEVEL A control is average pupil brightness of image A, and the LEVEL B control is the average pupil brightness of image B.

Figure 17:
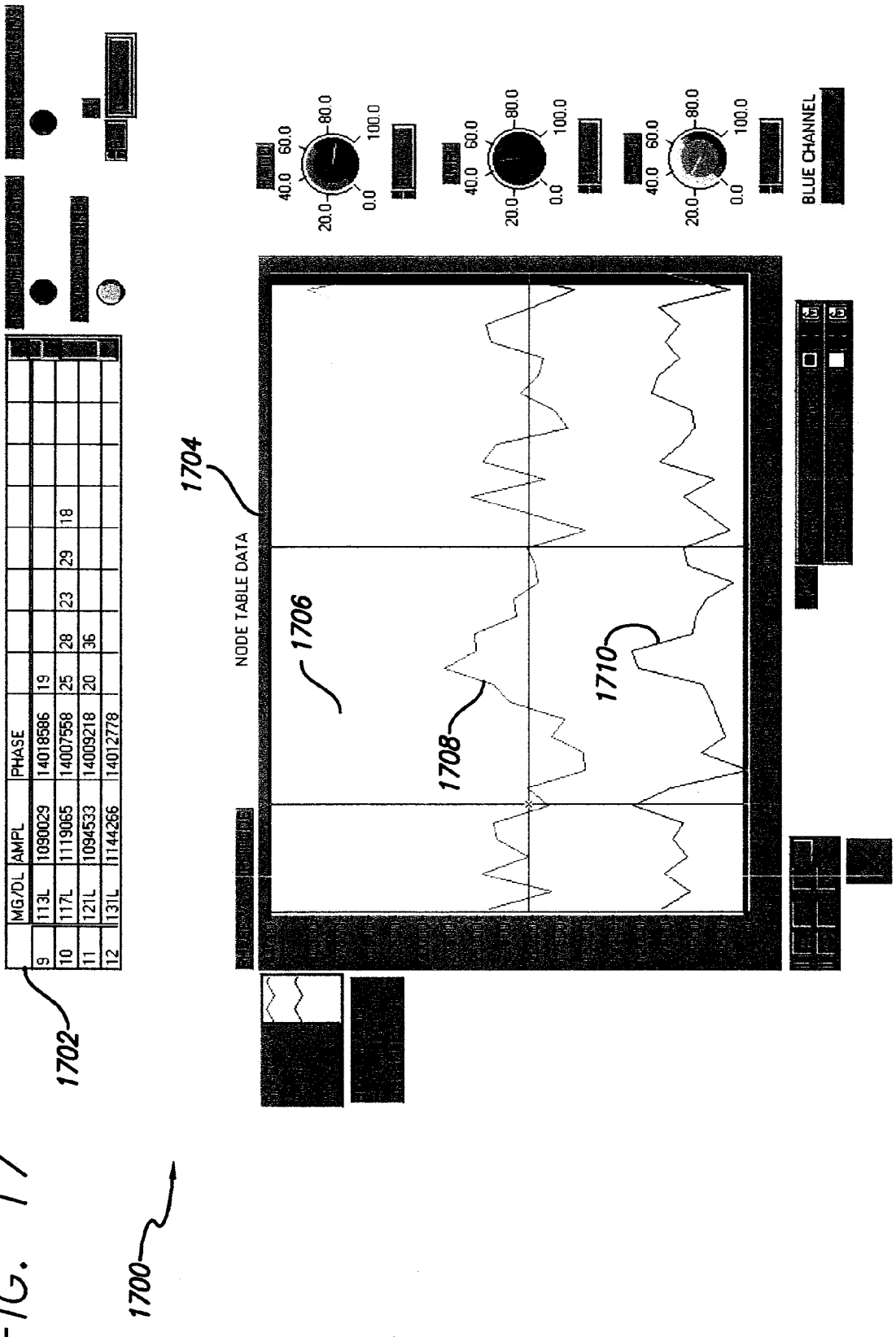
FIG. 17 displays another control panel for one embodiment of the invention.

FIG. 17 displays another control panel 1700 for one embodiment of the invention. This control panel displays a cousins table 1702. The cousins table has a column for a FRC number (frame cousin), a glucose level (MG/DL), an amplitude (AMPL), a phase angle (PHASE), and columns for eight cousins. The cousins were derived using the NODE TABLE DATA graph 1704. The NODE TABLE DATA graph is a graph of phase angle versus amplitude. The top line 1706 in the graph plots the ratio of phase angle to amplitude. The middle line 1708 plots amplitude, and the bottom line 1710 plots phase angle. The cousin nodes in the Cousin table 1702 are nodes that are at approximately the same horizontal axis on the plot of the ratio. For example, for FRC 10, the cousins are FRC 25, FRC 28, FRC 23, FRC 29, and FRC 18. Each of these frame cousins has a similar phase angle to amplitude ratio.

FIG. 18 is illustrates various Phase/Amplitude lookup tables that have been calibrated for different settings. For example, in the LOW NODES ALC table, LOW NODES refers to low brightness and ALC indicates that automatic level control was used. HIGH NODES indicates that there was high brightness. The BASE refers to a base line table that was calibrated with either a SMALL range of values or a LARGE (or all) range of values. DOUBLE FILTER indicates that two filters were set. COUSINS indicates that the cousins table was used.

Figure 19:
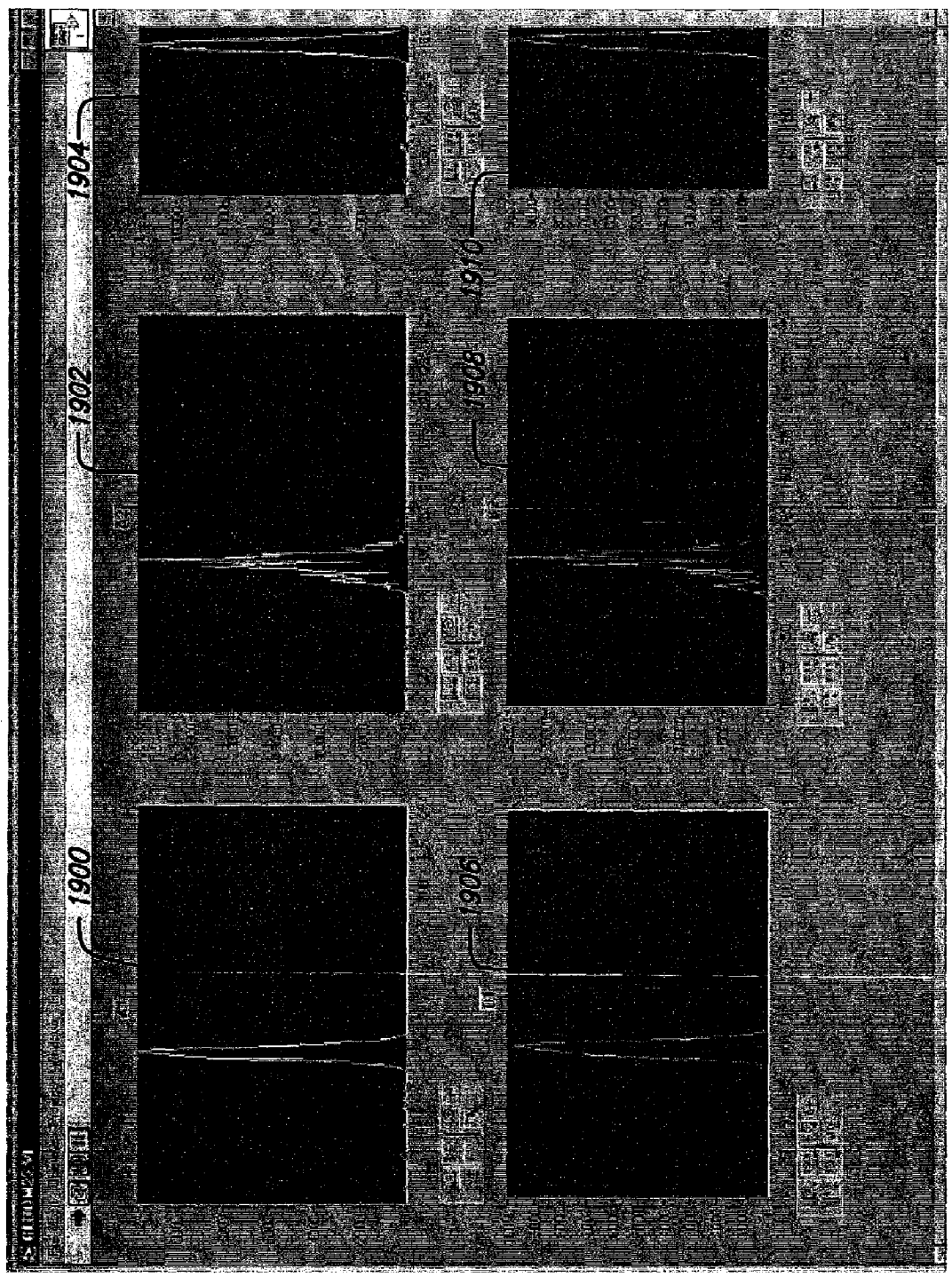
FIG. 19 displays histograms for Image A and Image B.

FIG. 19 displays histograms for Image A and Image B. The A1 histogram 1900 reflects Image A after a low pass filter has been applied. The A2 histogram 1902 reflects Image A before the low pass filter. The A3 histogram 1904 reflects Image A after a gamma stretch (If enabled). The B1 histogram 1906 reflects Image B after a low pass filter has been applied. The B2 histogram 1908 reflects Image B before the low pass filter. The B3 histogram 1910 reflects Image B after a gamma stretch (If enabled).

D.3 Flow Diagram and Alternative Embodiments

Figure 20A:
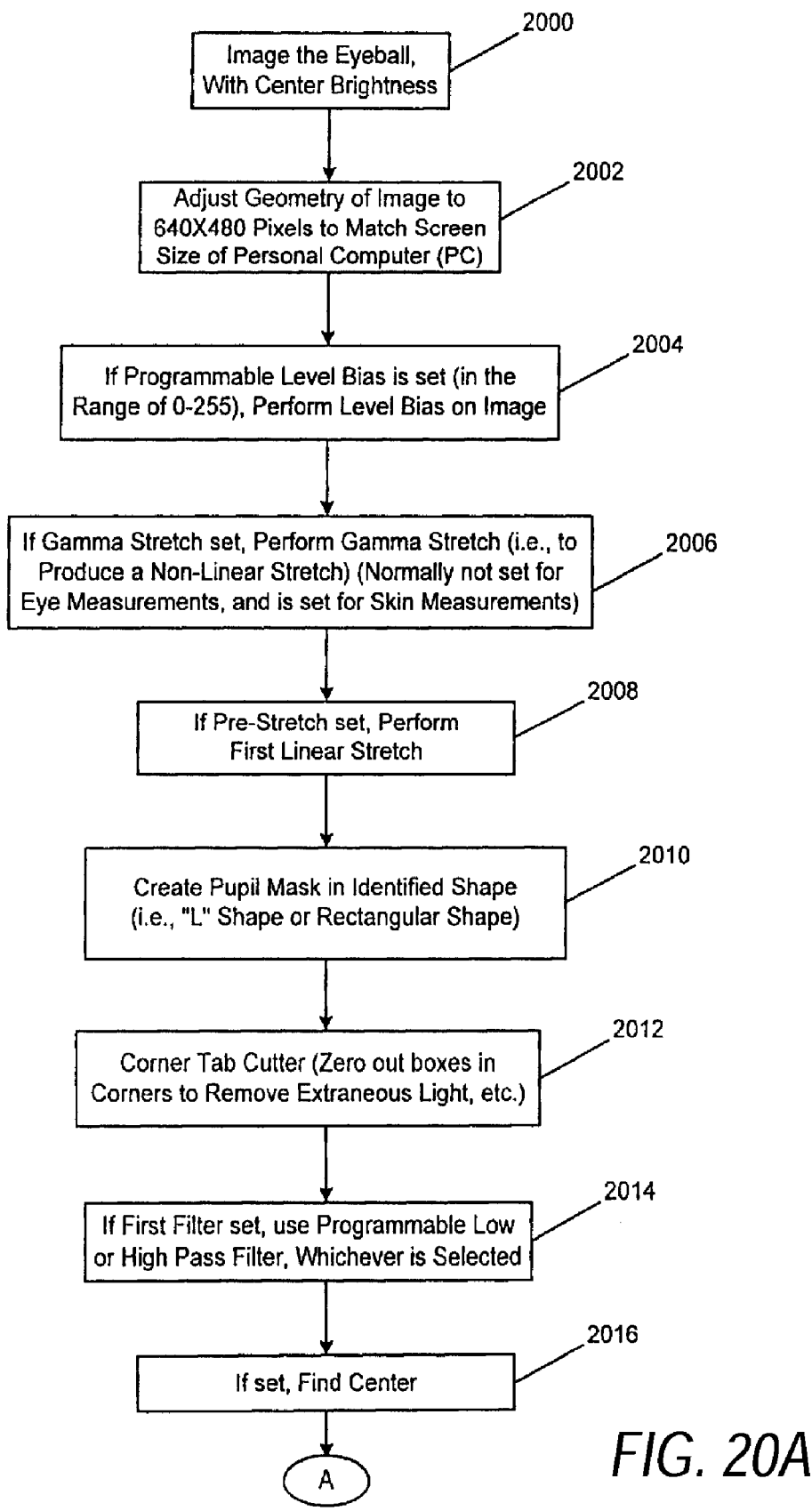
FIGS. 20A-20C are a flow diagram illustrating the steps performed by the noninvasive measurement system in one embodiment of the invention.
Figure 20B:
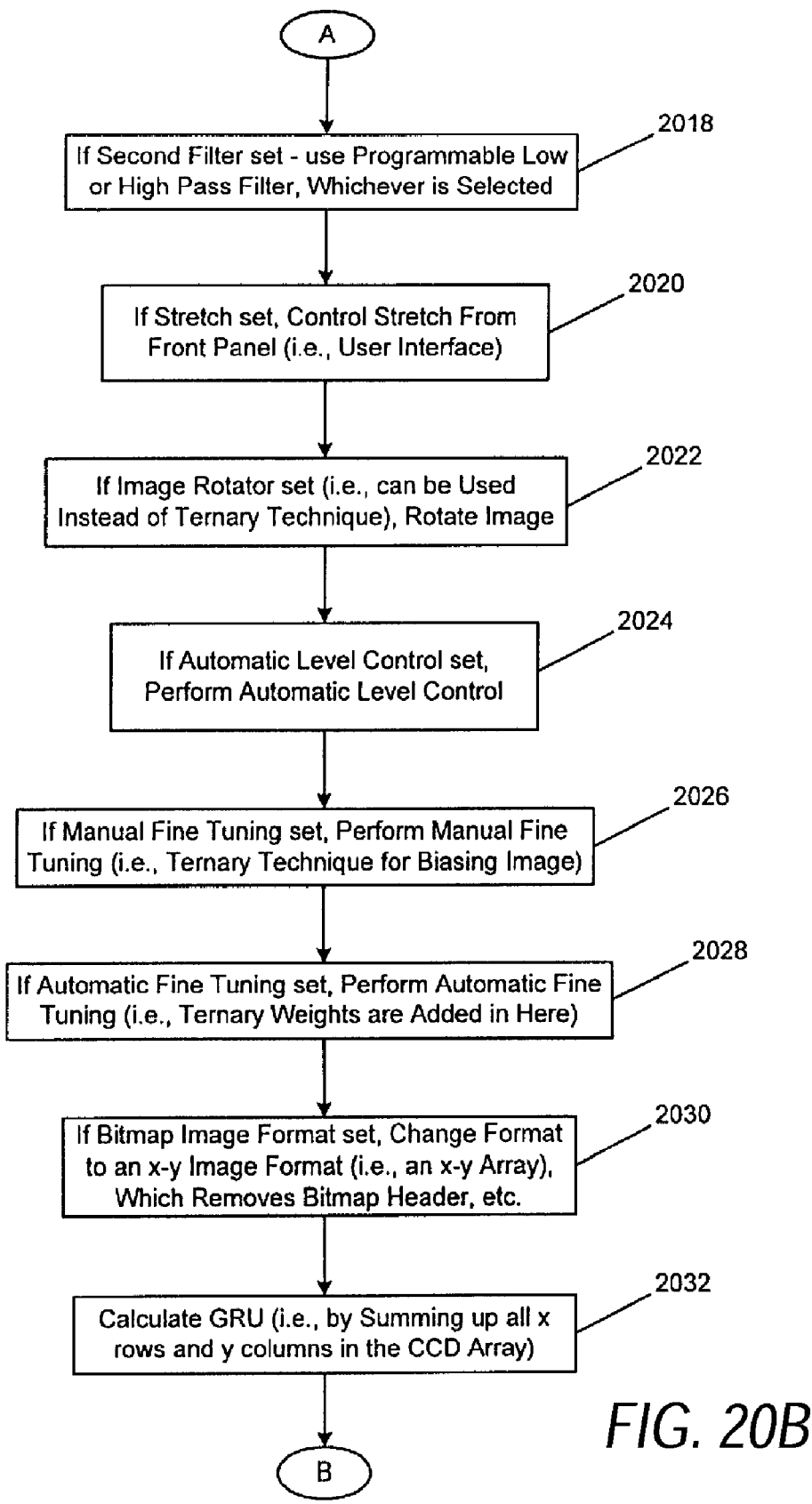
Figure 20C:
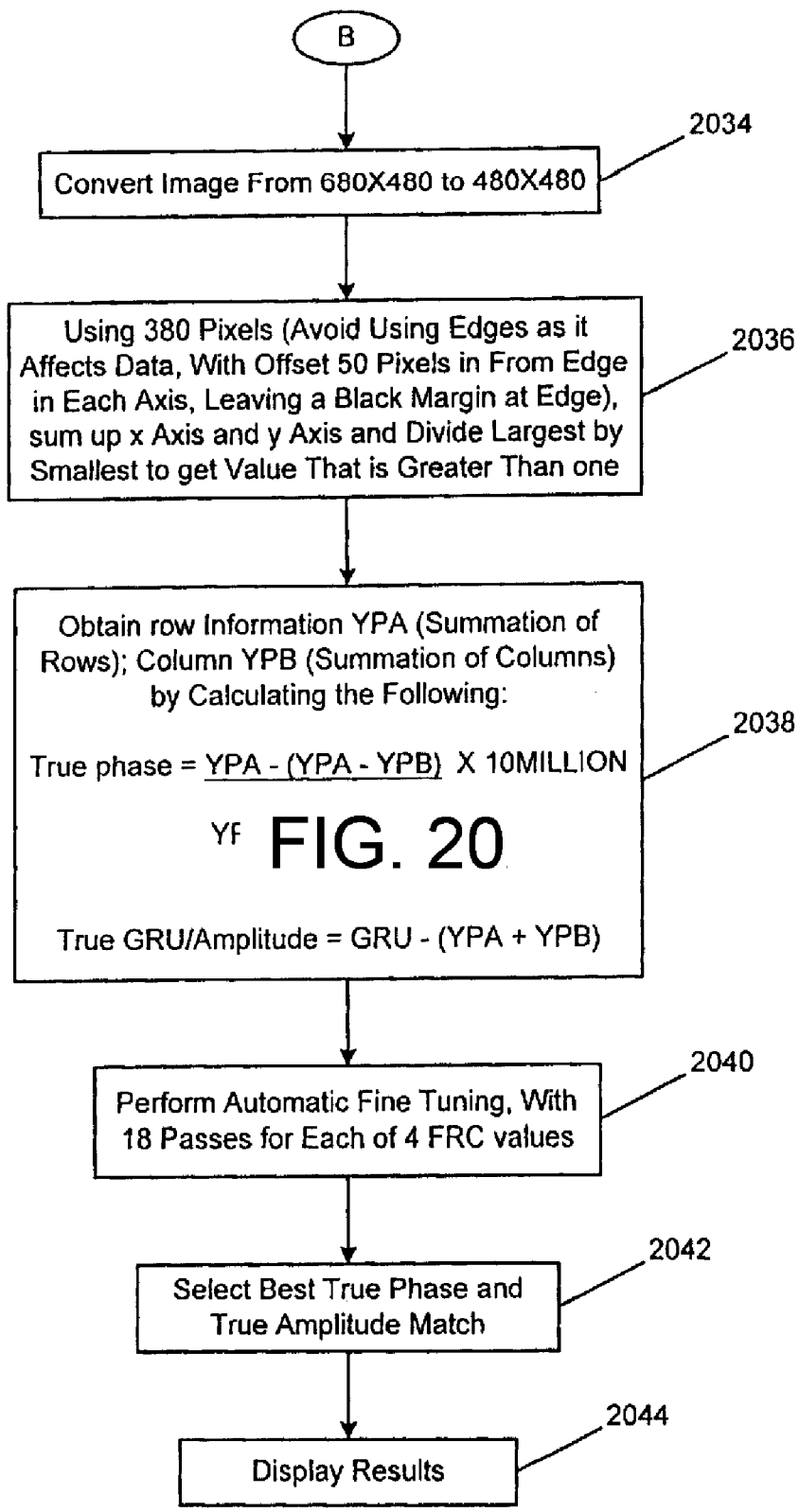

FIGS. 20A-20C are a flow diagram illustrating the steps performed by the noninvasive measurement system in one embodiment of the invention. In block 2000, the noninvasive measurement system images the eyeball, with center brightness. In block 2002, the noninvasive measurement system adjusts the geometry of the image to 640×480 pixels to match a screen size of a personal computer(PC). In block 2004, if programmable level bias is set (in the range of 0-255), the noninvasive measurement system performs level bias on the image. In block 2006, if gamma stretch is set, the noninvasive measurement system performs gamma stretch (i.e., a to produce a non-linear stretch). The gamma stretch is normally not set for eye measurements, and is set for skin measurements.

In block 2008, if pre-stretch set, the noninvasive measurement system performs a first linear stretch. In block 2010, the noninvasive measurement system creates a pupil mask in a specified shape. In one embodiment, a user may select either a "L" shape or a square shape. In other embodiments, an oval or circular shape may be provided, but it may require additional processing resources. In block 2012, corner tab cutter (zero out boxes in corners to remove extraneous light, etc.). In block 2014, if first filter set, the noninvasive measurement system uses either a programmable low or high pass filter, whichever is selected. In block 2016, if centering is set, the noninvasive measurement system finds the center. In block 2018, if second filter set, the noninvasive measurement system uses a programmable low or high pass filter, whichever is selected. In block 2020, if stretch set, the noninvasive measurement system controls stretch from input from the control panel. In block 2022, if image rotator is set, the noninvasive measurement system rotates the image (i.e., this can be used instead of Tenary technique).

In block 2024, if automatic level control is set, the noninvasive measurement system performs automatic level control. In block 2026, if manual fine tuning is set, the noninvasive measurement system performs manual fine tuning (i.e., Ternary technique for biasing image). In block 2028, if automatic fine tuning is set, the noninvasive measurement system performs automatic fine tuning (i.e., Ternary weights are added in here). In block 2030, if bitmap image format is set, the noninvasive measurement system changes format to an x-y image format (i.e., an x-y array), which removes the bitmap header, etc.

In block 2032, the noninvasive measurement system calculates GRU (i.e., by summing up all x rows and y columns in the image array). In block 2034, the noninvasive measurement system converts the image from 680×480 to 480×480 pixels. In block 2036, using 380 pixels (i.e., the noninvasive measurement system avoids using edges as it affects data, by offsetting 50 pixels in from edge in each axis, leaving a black margin at edge), the noninvasive measurement system sums up the x rows and y columns and divides the largest by the smallest to get a value that is greater than one. In block 2038, the noninvasive measurement system obtains row information YPA (summation of rows) and column information YPB (summation of columns) by calculating the following:

$$\text{true phase angle} = \frac{YPA - (YPA - YPB)}{YPB - (YPB - YPA)} \times 10 \text{ MILLION}$$

true GRU/amplitude=GRU-(YPA+YPB).

In block 2040, the noninvasive measurement system performs automatic fine tuning, with 18 passes for each of 4 FRC values. In block 2042, the noninvasive measurement system selects best true phase angle and true amplitude match. In block 2046, the noninvasive measurement system displays results.

The embodiment of the invention described in section D may be modified without exceeding the scope of the invention. For example, the technique of the invention may be practiced in a networked environment, as described with respect to FIG. 2.

E. Noninvasive Measurement of Glucose Concentration in Skin, Blood, and Nail Beds The noninvasive measurement system can also measure glucose concentrations from skin (e.g., wrist or stomach), blood (e.g., a drop of blood on a tissue), or nail beds. For each of these cases, the noninvasive measurement system generally uses the technique described in Section D, in which a phase angle and amplitude are correlated to a glucose level.

When working with the skin, a lower light level is used (i.e., the eve absorbs more light). In particular, experimentation was successfully performed by using the noninvasive measurement device to transmit light waves onto a portion of the wrist. The wrist contains numerous blood vessels, which may contain glucose molecules that reflect the light waves. A CCD camera was used to receive the reflected light waves from the wrist and to form a matrix of pixels that represented the received light waves. Next, the noninvasive measurement system applied a gamma 1 stretch to the matrix of pixels. This refers to a logarithmic re-mapping technique that gives more contrast for lower level pixels (small pixel values) and less contrast for higher level pixels (large pixel values), resulting in better resolution in the lower end. The noninvasive measurement system then processed the "stretched" matrix of pixels to obtain a phase angle and amplitude. From the phase angle and amplitude, the noninvasive measurement system found a glucose level. It is to be understood that this process can be modified without exceeding the scope of the invention. For example, the controls of FIG. 16 may be set so that a pupil cutter is also applied prior to calculating the phase angle and amplitude.

Additional experimentation was successfully performed by using the noninvasive measurement device to take a picture of a portion of the stomach. In particular, experimentation was successfully performed by using the noninvasive measurement device to transmit light waves onto a portion of the stomach. The stomach contains numerous blood vessels, which may contain glucose molecules that reflect the light waves. A CCD camera was used to receive the reflected light waves from the stomach and to form a matrix of pixels that represented the received light waves. When this was done, a gamma 3 stretch was applied. This refers to a gamma stretch with a more gradual effect and that gives more contrast for lower level pixels (small pixel values) and less contrast for higher level pixels (large pixel values), resulting in better resolution in the lower end. The noninvasive measurement system then processed the "stretched" matrix of pixels to obtain a phase angle and amplitude. From the phase angle and amplitude, the noninvasive measurement system found a glucose level. It is to be understood that this process can be modified without exceeding the scope of the invention. For example, the controls of FIG. 16 may be set so that a pupil cutter is also applied prior to calculating the phase angle and amplitude.

Furthermore, experiments were performed with noninvasive measurement device against blood drops. The blood drop was either on a tissue or on a test strip that had been used to run a test on a conventional (one touch) glucose monitor. With the test strips, the blood drop spread from a center point and retreated at an edge, so there were two layers of blood at the perimeter. With test strips, better values were derived from testing the perimeter. The blood drop was tested as the skin was, in less light. In particular, experimentation was successfully performed by using the noninvasive measurement device to transmit light waves onto the blood, which may contain glucose molecules that reflect the light waves. A CCD camera was used to receive the reflected light waves from the blood drop and to form a matrix of pixels that represented the received light waves. The noninvasive measurement system then processed the matrix of pixels to obtain a phase angle and amplitude. From the phase angle and amplitude, the noninvasive measurement system found a glucose level. It is to be understood that this process can be modified without exceeding the scope of the invention. For example, the controls of FIG. 16 may be set so that a pupil cutter is applied prior to calculating the phase angle and amplitude.

Further experiments were performed with nail beds. In particular, experimentation was successfully performed by using the noninvasive measurement device to transmit light waves onto the blood, which may contain glucose molecules that reflect the light waves. A CCD camera was used to receive the reflected light waves from the blood drop and to form a matrix of pixels that represented the received light waves. An experimental mask was implemented to allow the program to "see" the tissue edge at the side of the fingernail. The noninvasive measurement system then processed the matrix of pixels to obtain a phase angle and amplitude. From the phase angle and amplitude, the noninvasive measurement system found a glucose level. That is, the portion of the image that was not masked was processed into GRU values and monotonic brightness gains were observed with increasing blood glucose. It is to be understood that this process can be modified without exceeding the scope of the invention. For example, the controls of FIG. 16 may be set so that a pupil cutter is also applied prior to calculating the phase angle and amplitude.

The above options for using the noninvasive measurement device are provided for illustration only. The noninvasive measurement system may also be used on other portions of a body (e.g., on a leg). Furthermore, although the discussion has used human experimentation, the techniques of the invention are applicable to other biological entities.

F. Conclusion

This concludes the description of an embodiment of the invention. The following describes some alternative embodiments for accomplishing the present invention. For example, any type of computer, such as a mainframe, minicomputer, or personal computer, or computer configuration, such as a time-sharing mainframe, local area network, or standalone personal computer, could be used with the present invention.

The foregoing description of an embodiment of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather only by the claims appended hereto.

What is claimed is:

1. A method of correlating captured wave data to a substance in a biological entity, comprising:
   receiving wave data reflected from the biological entity;
   forming a plurality of pixels based on the reflected wave data;
   determining an amplitude for the reflected wave data based on the plurality of pixels;
   determining a phase angle for the reflected wave data based on the plurality of pixels; and
   identifying a glucose level in the biological entity based on the amplitude and phase angle.

2. The method of claim 1, wherein the determination of the amplitude comprises calculating an integrated value.

3. The method of claim 1, wherein the biological entity is an eye.

4. The method of claim 3, wherein the step of determining the amplitude comprises integrating a portion of the plurality of pixels to form an integrated value; and
   the step of identifying the glucose level comprises correlating the amplitude and the phase angle to a glucose level in a look up table.

5. The method of claim 4, wherein the integrating step further comprises:
   forming a matrix with the plurality of pixels; and masking a portion of the matrix.

6. An apparatus for correlating captured wave data to a substance in a biological entity, comprising:
   means for receiving wave data reflected from the biological entity;
   means for forming a plurality of pixels based on the reflected wave data;
   means for determining an amplitude for the reflected wave data based on the plurality of pixels;
   means for determining a phase angle for the reflected wave data based on the plurality of pixels; and
   means for identifying a glucose level in the biological entity based on the amplitude and the phase angle.

7. The apparatus of claim 6, further comprising means for calculating an integrated value to obtain the amplitude.

8. The apparatus of claim 6, wherein the biological entity is an eye.

9. The apparatus of claim 8, wherein the means for determining the amplitude comprises means for integrating a portion of the plurality of pixels to form an integrated value;

and wherein the means for identifying the glucose level comprises means for correlating the amplitude and the phase angle to a glucose level in a look up table.

10. The apparatus of claim 9, wherein the means for integrating comprises:

means for forming a matrix with the plurality of pixels; and
means for masking a portion of the matrix.

11. An apparatus for correlating captured wave data to a substance in a biological entity, comprising:

a memory comprising a plurality of instructions; and
a processing system coupled to the memory and configured to execute the plurality of instructions to:
receive data corresponding with wave data reflected from the biological entity;
form a plurality of pixels based on the reflected wave data;
determine an amplitude for the reflected wave data based on the plurality of pixels;
determine a phase angle for the reflected wave data based on the plurality of pixels; and
identify a glucose level in the biological entity based on the amplitude and the phase angle.

12. The apparatus of claim 11, wherein the processing system is further configured to determine the amplitude by calculating an integrated value.

13. The apparatus of claim 11, wherein the processing system is further configured to:
determine the amplitude by integrating a portion of the plurality of pixels to form an integrated value; and
identify a glucose level by correlating the amplitude and the phase angle to a glucose level in a look up table.

14. The apparatus of claim 13, wherein the processing system is further configured to:
form a matrix with the plurality of pixels; and
mask a portion of the matrix.

15. The apparatus of claim 11, further comprising an image capture device coupled to the processing system, and the processing system is further configured to receive the data corresponding with the reflected wave data through the image capture device.

* * * * *